US008293868B2

(12) United States Patent
King et al.

(10) Patent No.: US 8,293,868 B2
(45) **Date of Patent: *Oct. 23, 2012**

(54) INSECTICIDAL POLYPEPTIDES AND METHODS OF USE THEREOF

(76) Inventors: Glenn F. King, Chapel Hill (AU); Brianna Sollod McFarland, Windsor, CO (US); Graham Nicholson, Chatswood West (AU); Simon Gunning, Auckland Central (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/007,841

(22) Filed: Jan. 17, 2011

(65) Prior Publication Data

US 2011/0237502 A1 Sep. 29, 2011

Related U.S. Application Data

(62) Division of application No. 12/074,950, filed on Mar. 7, 2008, now Pat. No. 7,880,060, and a division of application No. 11/267,815, filed on Nov. 4, 2005, now Pat. No. 7,354,993.

(60) Provisional application No. 60/625,297, filed on Nov. 4, 2004.

(51) Int. Cl.

| | |
|---|---|
| ***C07K 2/00*** | (2006.01) |
| ***C07K 1/00*** | (2006.01) |
| ***C12P 1/00*** | (2006.01) |
| ***C12N 1/00*** | (2006.01) |

(52) U.S. Cl. ....... 530/300; 435/69.1; 435/243; 435/267; 435/41; 530/858

(58) Field of Classification Search ........................ None
See application file for complete search history.

(56) References Cited

U.S. PATENT DOCUMENTS

| | | | | |
|---|---|---|---|---|
| 4,757,011 | A | 7/1988 | Chaleff et al. | |
| 4,769,061 | A | 9/1988 | Comai | |
| 4,855,405 | A | 8/1989 | Yoshioka et al. | |
| 4,879,236 | A | 11/1989 | Smith et al. | |
| 4,918,107 | A | 4/1990 | Nakajima et al. | |
| 4,940,835 | A | 7/1990 | Shah et al. | |
| 4,971,908 | A | 11/1990 | Kishore et al. | |
| 5,457,178 | A | 10/1995 | Jackson et al. | |
| 5,695,959 | A | 12/1997 | Jackson et al. | |
| 5,756,459 | A | 5/1998 | Jackson et al. | |
| 5,763,568 | A | 6/1998 | Atkinson et al. | |
| 6,096,304 | A | 8/2000 | McCutchen | |
| 6,521,454 | B1 | 2/2003 | Becnel et al. | |
| 6,583,264 | B2 | 6/2003 | King et al. | |
| 7,354,993 | B2 * | 4/2008 | King et al. | 530/300 |
| 7,880,060 | B2 | 2/2011 | King et al. | |
| 2004/0138423 | A1 | 7/2004 | King et al. | |

FOREIGN PATENT DOCUMENTS

| | | |
|---|---|---|
| WO | 95 01996 | 1/1995 |
| WO | 98 57988 | 12/1998 |

OTHER PUBLICATIONS

Altschul, "Basic Local Alignment Search Tool", J. Mol. Biol., 215 (1990), pp. 403-410.
Altschul, "Gapped BLAST and PSI-BLAST: A New Generation of Protein Database Search Programs", Nucleic Acids Res., 25 (1997), pp. 3389-3402.
Brogdon, "Insecticide Resistance and Vector Control", Emerging Infectious Diseases, 4 (1998).
Cory, "Field Trial of a Genetically Improved Baculovirus Insecticide", Nature, 370 (1994), pp. 138-140.
Derst, "The Large Conductance Ca2+-Activated Potassium Channel (pSIo) of the Cockroach Periplaneta Americana: Structure, Local . . . ", Eur. J. Neurosci, 17 (2003), pp. 1197-1212.
Dryløv, "Improved Prediction of Signal Peptides: SignalP 3.0", Journal of Molecular Biology, 340 (2004), pp. 783-795.
Eitan, "A Scorpion Venom Neurotoxin Paralytic to Insects that Affects Sodium Current inactivitaton:? Purification, Primary Structure, . . . "; Biochem., 29 (1990), pp. 5941-5947.
Feyereisen, "Molecular Biology of Insecticide Resistance", Toxicology Letters, 82/83 (1995), pp. 83-90.
Fitches, "Fusion Proteins Containing Insect-Specific Toxins as Pest Control Agents: Snowdrop Lectin Delivers Fused Insecticidal . . . " J. of Insect. Phy., 50 (2004), pp. 61-71.
Fletcher, "The Structure of a Novel Insecticidal Neurotoxin, Omega-Atracotoxin-HV1, from the Venom of an Australian Funnel Web Spider", Nature Struct.Bio., 4 (1997) pp. 559-566.
Fourgoux-Nicol et al. 1999, Plant Molecular Biology 40: 857-872.
Frohman, "Rapid Production of Full-Length cDNAs from Rare Transceipts: Amplication Using a Single Gene-Specific Oligonucleotide Primer", Proc. Natl. Acad. Sci. USA, 85 (1988), pp. 8993-9002.
Fromm, "Expression of Genes Transferred into Monocot and Dicot Plant Cells by Electroporation", Proc. Natl. Acad. Sci. USA, 82 (1985), pp. 5824-5828.
Gubler, "Resurgent Vector-Born Diseases as a Global Health Problem", Emerging Infectious Diseases, 4 (1998), p. 10.
Heinrich, "A repressible Female-Specific Lethal Genetic System for making Transgenic Insect Strains Suitable for a Sterile-Release Program", Proc. Natl. Acad. Sci. USA, 97 (2000), pp. 8229-8232.
Jackson, "Spider Toxins: Recent Applications in Neurobiology", Annual Reviews of Neuroscience, 12 (1989), pp. 405-414.
Karlin, "Methods of Assessing the Statistical Significance of Molecular Sequence Features by Using General Scoring Schemes", Proc. Natl. Acad. Sci., USA, 87 (1990), p. 2264-2268.
Lazar et al. Mol. Cell. Biol., vol. 8, pp. 1247-1252, 1988.

(Continued)

*Primary Examiner* — Medina A Ibrahim

(74) *Attorney, Agent, or Firm* — Honigman Miller Schwartz & Cohn LLP; Thomas A. Wootton; Jonathan P. O'Brien

(57) ABSTRACT

A family of insecticidal polypeptides expressed in the venom gland of spiders of the genera *Atrax* and *Hadronyche* have been described. Also included are polynucleotides and expression vectors encoding the polypeptides and insect viruses and cells expressing the polypeptides. Transgenic plants and insects expressing the insecticidal polypeptides are also described. The insecticidal polypeptides may be employed in methods and compositions for treating insects, insect larvae, and plants.

8 Claims, 5 Drawing Sheets

OTHER PUBLICATIONS

Logan, "Adenovirus Tripartite Leader Sequence Enhances Translation of mRNAs Late After Infection", Proc. Nat. Acad. Sci. USA, 81 (1984), pp. 3655-3659.

Lowy, "Isolation of Transforming DNA": Cloning the Hamster Aprt Gene, Cell, 22 (1980), pp. 817-823.

Maggio, "Scanning Mutagenesis of a Janus-Faced Atracotoxin Reveals a Bipartite Surface Patch that is Essential for Neurotoxic Function", J. Biol. Chem, 277 (2002), pp. 22806-22813.

McCutchen, "Development of a Recombinant Baculovirus Expressing an Insect-Selective Neurotoxin: Potential for Pest Control", Bio/Technology, 9 (1991), pp. 848-851.

Riley, "Cloning, Experssion and Spectroscopic Studies of the Jun Leucine Zipper Domain", Eur. J. Biochem, 219 (1994), pp. 877-886.

Sollod, Were arachnids the First to Use combinatorial Peptide Libraries?, Peptides, 26 (2005), pp. 131-139.

Stewart, "Construction of an Improved Baculovirus Insecticide Containing an Insect-Specific Toxin Gnee" Nature, 352 (1991), pp. 85-88.

Szybalska, "Genetics of Human Cell lines, IV. DNA-Mediated Heritabale Transformation of a Biochemical Trait", Proc. Natl. Acad. Sci. USA, 48 (1962), pp. 2026-2034.

Tedford, "Functional Significance of the Beta Hairpin in the Insecticidal Neurotoxin Omega-Atracotoxin-Hv1a", J. Biol. Chem, (2001), pp. 26568-26576.

Tedford, "Australian Funnel-Web Spiders: Master Insecticide Chemists", Toxicon, 43 (2004), pp. 601-618.

Thomas, "Insect Population Control Using a Dominant, Repressible, Lethal Genetic System", Sicence, 287 (2000), pp. 2474-2476.

Toenniessen, "Advances in Plant Biotechnology and its Adoption in Developing countries", Current Opinion in Plant Biology, 6 (2003), pp. 191-198.

Wang, "Discovery and Structure of a Potent and Highly Specific blocker of Insect Calcium Channels", J. Biol. Chem., 276 (2001), pp. 40806-40812.

Wang, "Discovery and Characterization of a Family of Insecticial Neurotoxins with a rare Vicinal Disulfide Bridge", Nature Structural Biology, 7 (2000), pp. 505-513.

Wang, "Structure-Function Studies of -Atracotoxin, a Potent Antagonist of Insect Voltage-Gated Calcium Channels", Eur. J. Biochem., 264 (1999), pp. 488-494.

Wigler, "Transfer of Purified Herpes Virus Thymidine Kinase Gene to Cultured Mouse Cells", Cell, 11 (1977), pp. 223-232.

Yang, "Maize Sucrose Synthase-1 Promoter Directs Phloem Cell-Specific Expression of Gus Gene in Transgenic Tobacco Plants", Proc. Natl. Acad. Sci. USA, 87 (1990), pp. 4144-4148.

Database UniProt [online]; Omega-Missulenatoxin-Mb1a (Omega-MSTX-Mb1a), (2003); XP002384404 as cited in International Publication No. WO 2006/052806.

Database UniProt [online]; Omega-Atracotoxin-Aria (0mega-AcTx-Ar1a); (2003); XP002384405 as cited in International Publication No. WO 2006/052806.

International Search Report; for International Application No. PCT/US2005/040139, International Publication No. WO 2006/052806.

Tomalski, "Insect Paralysis by Baculovirus-Mediated Expression of a Mite Neurotoxin Gene", Nature, 352 (1991), pp. 82-85.

* cited by examiner

FIGURE 1: SEQUENCE ALIGNMENT OF U-ACTX PREPROPEPTIDE SEQUENCES

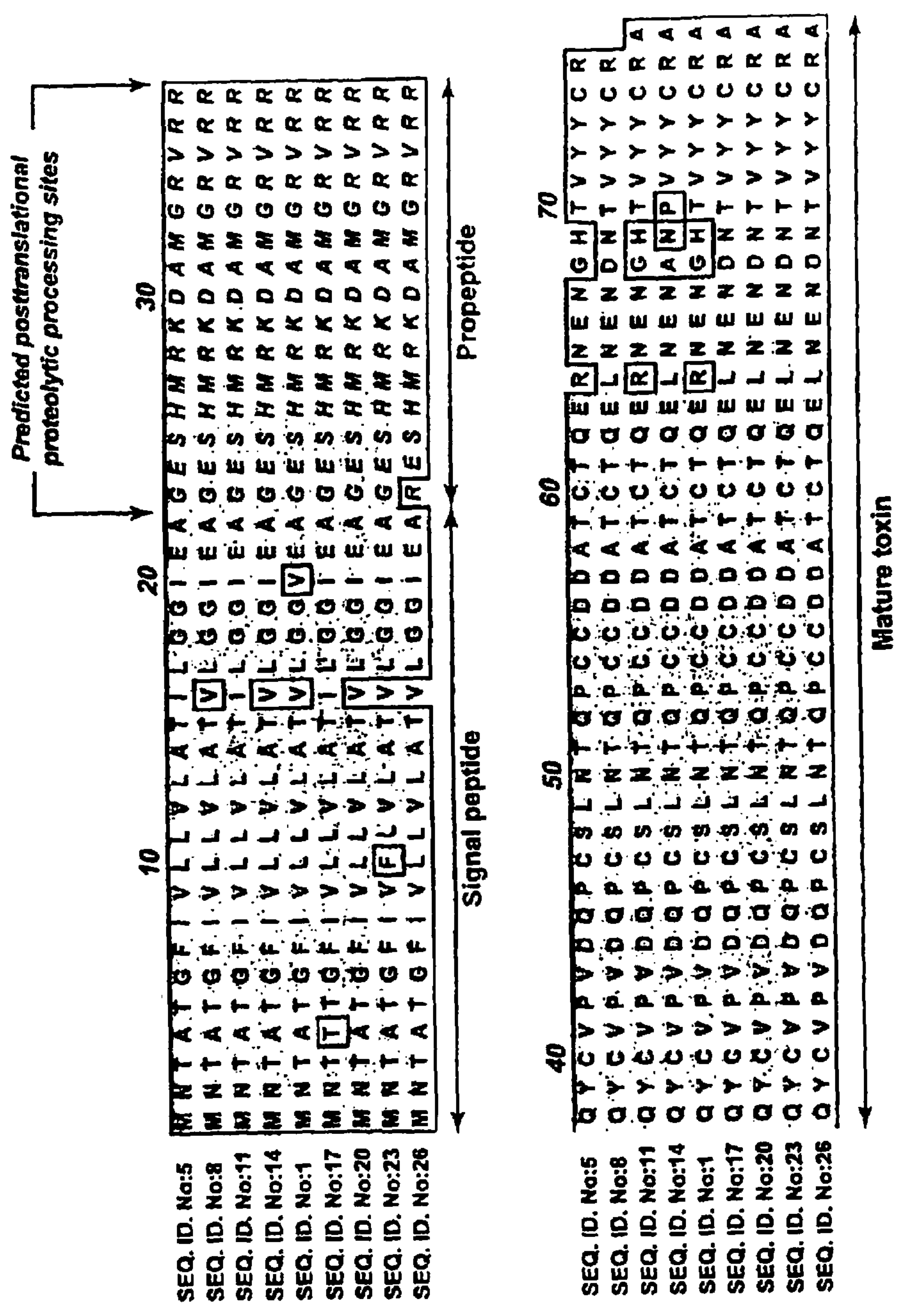

| | | |
|---|---|---|
| SEQ. ID. No:5 | MNTATGFIVLLLVLATLLGGIEAGESHMRKDAMGRVRR | |
| SEQ. ID. No:8 | MNTATGFIVLLLVLATLLGGIEAGESHMRKDAMGRVRR | |
| SEQ. ID. No:11 | MNTATGFIVLLLVLATLLGGIEAGESHMRKDAMGRVRR | |
| SEQ. ID. No:14 | MNTATGFIVLLLVLATLLGGIEAGESHMRKDAMGRVRR | |
| SEQ. ID. No:1 | MNTATGFIVLLLVLATLLGGVEAGESHMRKDAMGRVRR | |
| SEQ. ID. No:17 | MNTATGFIVLLLVLATVLGGIEAGESHMRKDAMGRVRR | |
| SEQ. ID. No:20 | MNTATGFIVLLLVLATVLGGIEAGESHMRKDAMGRVRR | |
| SEQ. ID. No:23 | MNTATGFIVLLLVLATVLGGIEAGESHMRKDAMGRVRR | |
| SEQ. ID. No:26 | MNTATGFIVLLLVLATVLGGIEARESHMRKDAMGRVRR | |

Signal peptide — Propeptide — Predicted posttranslational proteolytic processing sites

| | |
|---|---|
| SEQ. ID. No:5 | QYCVPVDQPCSLNTQPCCDDATCTQERNENGHTVYYCR A |
| SEQ. ID. No:8 | QYCVPVDQPCSLNTQPCCDDATCTQELNENDNTVYYCR A |
| SEQ. ID. No:11 | QYCVPVDQPCSLNTQPCCDDATCTQERNENGHTVYYCR A |
| SEQ. ID. No:14 | QYCVPVDQPCSLNTQPCCDDATCTQELNENAHTVYYCR A |
| SEQ. ID. No:1 | QYCVPVDQPCSLNTQPCCDDATCTQELNENANPTVYYCR A |
| SEQ. ID. No:17 | QYCVPVDQPCSLNTQPCCDDATCTQERNENGHTVYYCR A |
| SEQ. ID. No:20 | QYCVPVDQPCSLNTQPCCDDATCTQELNENDNTVYYCR A |
| SEQ. ID. No:23 | QYCVPVDQPCSLNTQPCCDDATCTQELNENDNTVYYCR A |
| SEQ. ID. No:26 | QYCVPVDQPCSLNTQPCCDDATCTQELNENDNTVYYCR A |

Mature toxin

FIGURE 2: CONSTRUCTION OF A SYNTHETIC GENE ENCODING U-ACTX-Hv1a
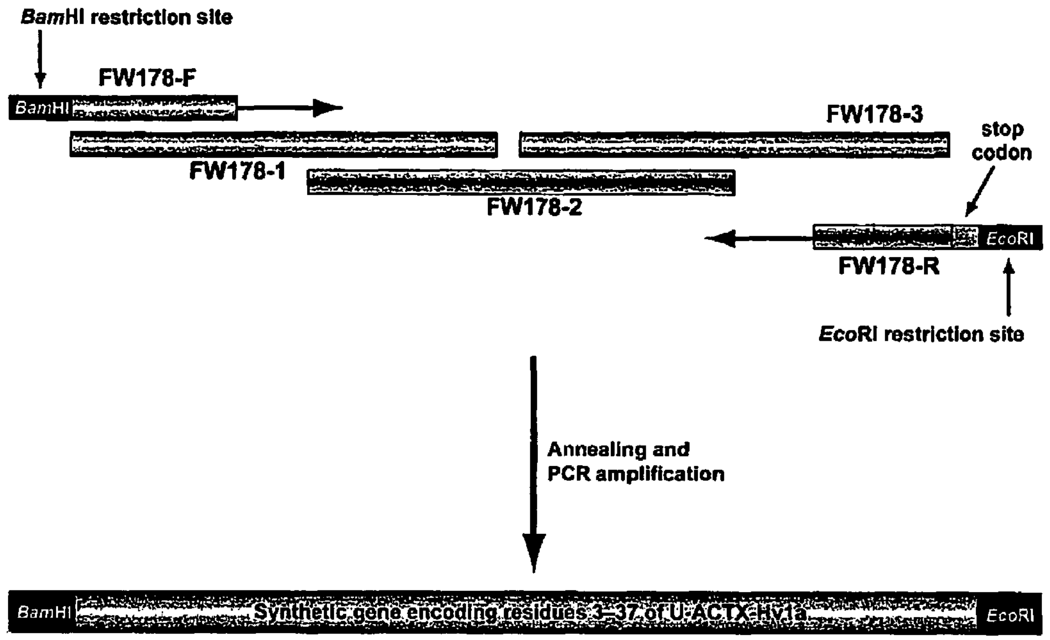

FIGURE 3: DOSE-RESPONSE CURVE FOR rU-ACTX-Hv1a IN HOUSE FLIES
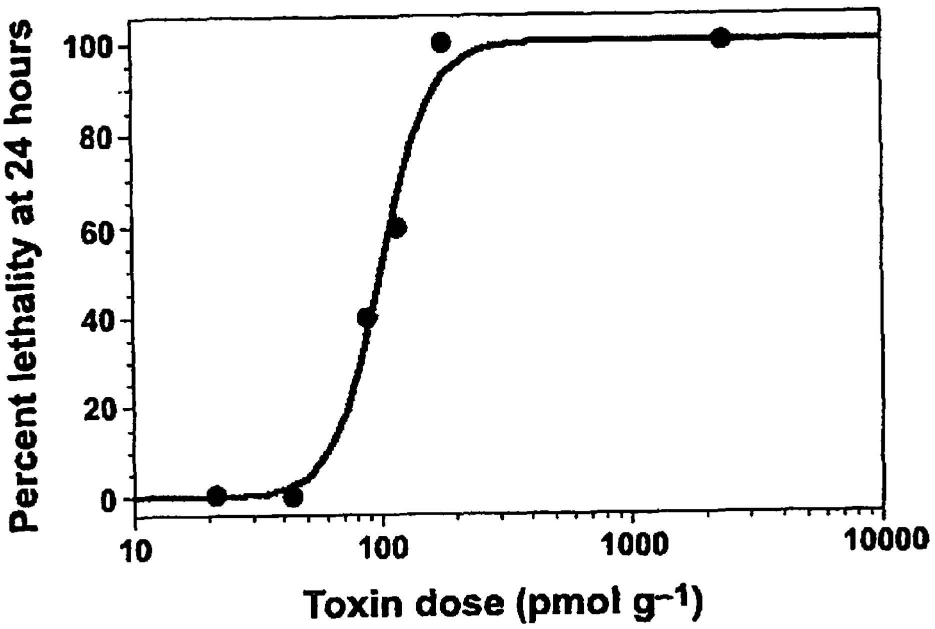

FIGURE 4: CONCENTRATION-DEPENDENCE OF THE INHIBITION OF VOLTAGE-GATED CALCIUM CHANNEL CURRENTS IN COCKROACH DUM NEURONS BY rU-ACTX-Hv1a
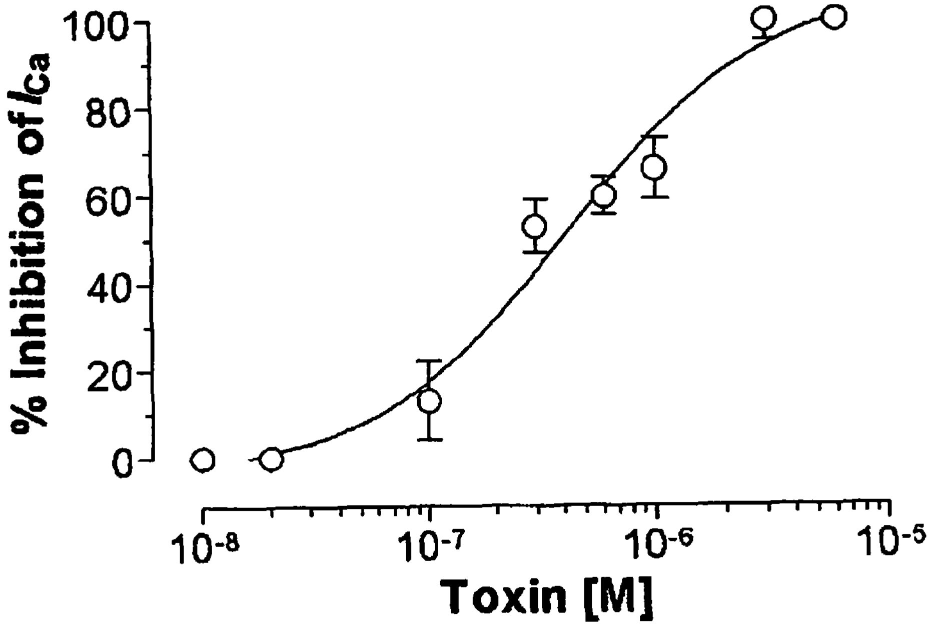

FIGURE 5: CONCENTRATION-DEPENDENCE OF THE INHIBITION OF WHOLE-CELL CALCIUM-ACTIVATED POTASSIUM CHANNEL CURRENTS IN HEK293 CELLS EXPRESSING THE COCKROACH pSLO CHANNEL
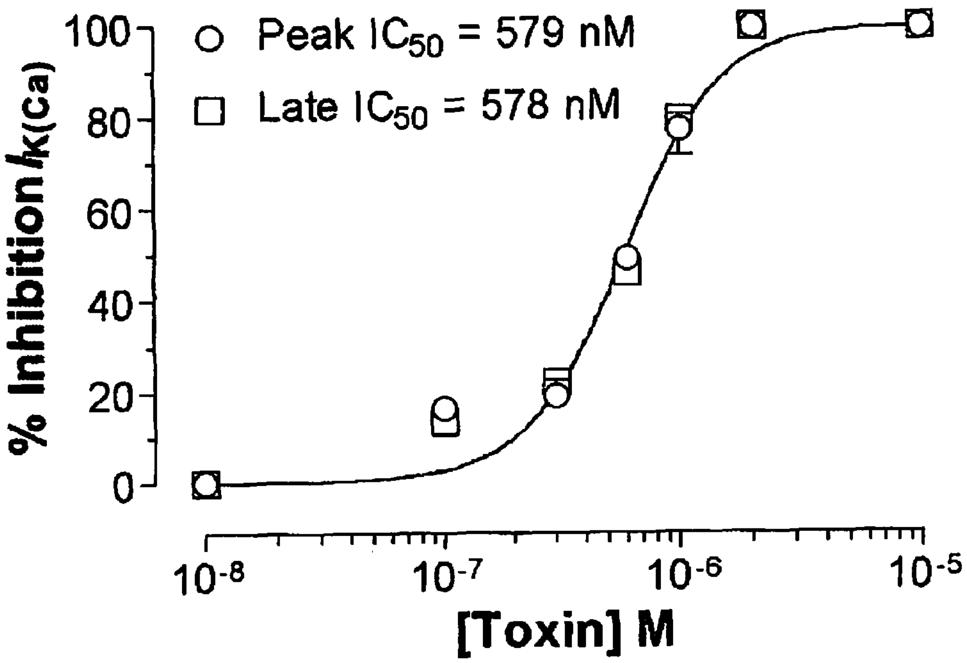

SEQUENCE LISTING

```
<160> NUMBER OF SEQ ID NOS: 39

<210> SEQ ID NO 1
<211> LENGTH: 76
<212> TYPE: PRT
<213> ORGANISM: Hadronyche versuta

<400> SEQUENCE: 1

Met Asn Thr Ala Thr Gly Phe Ile Val Leu Leu Val Leu Ala Thr Val
1               5                   10                  15

Leu Gly Gly Val Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Arg
    50                  55                  60

Asn Glu Asn Gly His Thr Val Tyr Tyr Cys Arg Ala
65                  70                  75


<210> SEQ ID NO 2
<211> LENGTH: 39
<212> TYPE: PRT
<213> ORGANISM: Hadronyche versuta

<400> SEQUENCE: 2

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg Ala
        35


<210> SEQ ID NO 3
<211> LENGTH: 39
<212> TYPE: PRT
<213> ORGANISM: Hadronyche versuta

<400> SEQUENCE: 3

Gly Ser Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg Ala
        35


<210> SEQ ID NO 4
<211> LENGTH: 228
<212> TYPE: DNA
<213> ORGANISM: Hadronyche versuta

<400> SEQUENCE: 4
```

-continued

```
atgaataccg caacaggttt catcgtcctt ttggttttgg cgacagttct aggaggagtt     60

gaagcaggag aatctcatat gagaaaagat gccatgggaa gagttcgtcg acaatattgc    120

gttccagttg atcaaccgtg ctccctgaat acccaaccgt gctgcgatga tgccacgtgc    180

acacaagagc ggaatgaaaa cggccacact gtttattatt gcagggct                 228


<210> SEQ ID NO 5
<211> LENGTH: 75
<212> TYPE: PRT
<213> ORGANISM: Hadronyche versuta

<400> SEQUENCE: 5

Met Asn Thr Ala Thr Gly Phe Ile Val Leu Leu Val Leu Ala Thr Ile
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Arg
    50                  55                  60

Asn Glu Asn Gly His Thr Val Tyr Tyr Cys Arg
65                  70                  75


<210> SEQ ID NO 6
<211> LENGTH: 38
<212> TYPE: PRT
<213> ORGANISM: Hadronyche versuta

<400> SEQUENCE: 6

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg
        35


<210> SEQ ID NO 7
<211> LENGTH: 225
<212> TYPE: DNA
<213> ORGANISM: Hadronyche versuta

<400> SEQUENCE: 7

atgaataccg caacaggttt catcgtcctt ttggttttgg cgacaattct cggaggtatt     60

gaagcaggag aatctcatat gagaaaagat gccatgggaa gagttcgtcg acaatattgc    120

gttccagttg atcaaccgtg ctctctgaat acccaaccgt gctgcgatga tgccacgtgc    180

acacaagagc ggaatgaaaa cggccacact gtttattatt gcagg                    225


<210> SEQ ID NO 8
<211> LENGTH: 75
<212> TYPE: PRT
<213> ORGANISM: Hadronyche versuta

<400> SEQUENCE: 8

Met Asn Thr Ala Thr Gly Phe Ile Val Leu Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
```

```
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg
65                  70                  75


<210> SEQ ID NO 9
<211> LENGTH: 38
<212> TYPE: PRT
<213> ORGANISM: Hadronyche versuta

<400> SEQUENCE: 9

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg
        35


<210> SEQ ID NO 10
<211> LENGTH: 225
<212> TYPE: DNA
<213> ORGANISM: Hadronyche versuta

<400> SEQUENCE: 10

atgaataccg caacaggttt catcgtcctt ttggttttgg cgacagttct cggaggtatt      60

gaagcaggag aatctcatat gagaaaagat gccatgggaa gagttcgtcg acaatattgc     120

gttccagttg atcaaccgtg ctctctgaat acccaaccgt gctgcgatga tgccacgtgc     180

acacaagaac taaatgaaaa cgacaacact gtttattatt gcagg                     225


<210> SEQ ID NO 11
<211> LENGTH: 76
<212> TYPE: PRT
<213> ORGANISM: Hadronyche versuta

<400> SEQUENCE: 11

Met Asn Thr Ala Thr Gly Phe Ile Val Leu Leu Val Leu Ala Thr Ile
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Arg
    50                  55                  60

Asn Glu Asn Gly His Thr Val Tyr Tyr Cys Arg Ala
65                  70                  75


<210> SEQ ID NO 12
<211> LENGTH: 39
<212> TYPE: PRT
<213> ORGANISM: Hadronyche versuta

<400> SEQUENCE: 12

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Arg Asn Glu Asn Gly His
            20                  25                  30

Thr Val Tyr Tyr Cys Arg Ala
        35
```

<210> SEQ ID NO 13
<211> LENGTH: 228
<212> TYPE: DNA
<213> ORGANISM: Hadronyche versuta

<400> SEQUENCE: 13

```
atgaataccg caacaggttt catcgtcctt ttggttttgg cgacaattct cggaggtatt      60

gaagcaggag aatctcatat gagaaaagac gccatgggaa gagttcgtcg acaatattgc     120

gttccagttg atcaaccgtg ctctctgaat acccaaccgt gctgcgatga tgccacgtgc     180

acacaagagc ggaatgaaaa cggccacact gtttattatt gcagggct                 228
```

<210> SEQ ID NO 14
<211> LENGTH: 76
<212> TYPE: PRT
<213> ORGANISM: Hadronyche versuta

<400> SEQUENCE: 14

```
Met Asn Thr Ala Thr Gly Phe Ile Val Leu Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Ala Asn Pro Val Tyr Tyr Cys Arg Ala
65                  70                  75
```

<210> SEQ ID NO 15
<211> LENGTH: 39
<212> TYPE: PRT
<213> ORGANISM: Hadronyche versuta

<400> SEQUENCE: 15

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Ala Asn
            20                  25                  30

Pro Val Tyr Tyr Cys Arg Ala
        35
```

<210> SEQ ID NO 16
<211> LENGTH: 228
<212> TYPE: DNA
<213> ORGANISM: Hadronyche versuta

<400> SEQUENCE: 16

```
atgaataccg caacaggttt catcgtcctt ttggttttgg cgacagttct cggaggtatt      60

gaagcaggag aatctcatat gagaaaagat gccatgggaa gagttcgtcg ccaatattac     120

gttccagttg atcaaccgtg ctctttgaat acccaaccgt gctgcgatga tgccacgtgc     180

acccaagagc taaatgaaaa cgccaaccct gtttattatt gcagggct                 228
```

<210> SEQ ID NO 17
<211> LENGTH: 76
<212> TYPE: PRT
<213> ORGANISM: Hadronyche versuta

<400> SEQUENCE: 17

```
Met Asn Thr Thr Thr Gly Phe Ile Val Leu Leu Val Leu Ala Thr Ile
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75


<210> SEQ ID NO 18
<211> LENGTH: 39
<212> TYPE: PRT
<213> ORGANISM: Hadronyche versuta

<400> SEQUENCE: 18

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35


<210> SEQ ID NO 19
<211> LENGTH: 228
<212> TYPE: DNA
<213> ORGANISM: Hadronyche versuta

<400> SEQUENCE: 19

atgaatacca caacaggttt catcgtcctt ttggttttgg cgacaattct cggaggtatt      60

gaagcaggag aatctcatat gagaaaagat gccatgggaa gagttcgtcg acaatattgc     120

gttccagttg atcaaccgtg ctctctgaat acccaaccgt gctgcgatga tgccacgtgc     180

acacaagagc taaatgaaaa cgacaacact gtttattatt gcagggct                  228


<210> SEQ ID NO 20
<211> LENGTH: 76
<212> TYPE: PRT
<213> ORGANISM: Hadronyche versuta

<400> SEQUENCE: 20

Met Asn Thr Ala Thr Gly Phe Ile Val Leu Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75


<210> SEQ ID NO 21
<211> LENGTH: 39
<212> TYPE: PRT
<213> ORGANISM: Hadronyche versuta

<400> SEQUENCE: 21
```

```
Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35


<210> SEQ ID NO 22
<211> LENGTH: 228
<212> TYPE: DNA
<213> ORGANISM: Hadronyche versuta

<400> SEQUENCE: 22

atgaataccg caacaggttt catcgtcctt ttggttttgg cgacagttct cggaggtatt      60

gaagcaggag aatctcatat gagaaaagat gccatgggaa gagttcgtcg acaatattgc     120

gttccagttg atcaaccgtg ctctctgaat acccaaccgt gctgcgatga tgccacgtgc     180

acacaagaac taaatgaaaa cgacaacact gtttattatt gcagggct                  228


<210> SEQ ID NO 23
<211> LENGTH: 76
<212> TYPE: PRT
<213> ORGANISM: Hadronyche versuta

<400> SEQUENCE: 23

Met Asn Thr Ala Thr Gly Phe Ile Val Phe Leu Val Leu Ala Thr Val
1               5                   10                  15

Leu Gly Gly Ile Glu Ala Gly Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75


<210> SEQ ID NO 24
<211> LENGTH: 39
<212> TYPE: PRT
<213> ORGANISM: Hadronyche versuta

<400> SEQUENCE: 24

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35


<210> SEQ ID NO 25
<211> LENGTH: 228
<212> TYPE: DNA
<213> ORGANISM: Hadronyche versuta

<400> SEQUENCE: 25

atgaataccg caacaggttt catcgtcttt ttggttttgg cgacagttct cggaggtatt      60

gaagcaggag aatctcatat gagaaaagat gccatgggaa gagttcgtcg acaatattgc     120

gttccagttg atcaaccgtg ctctctgaat acccaaccgt gctgcgatga tgccacgtgc     180

acacaagaac taaatgaaaa cgacaacact gtttattatt gcagggct                  228
```

<210> SEQ ID NO 26
<211> LENGTH: 76
<212> TYPE: PRT
<213> ORGANISM: Atrax robustus

<400> SEQUENCE: 26

Met Asn Thr Ala Thr Gly Phe Ile Val Leu Leu Val Leu Ala Thr Val
1               5                   10                  15

Leu Gly Gly Ile Glu Ala Arg Glu Ser His Met Arg Lys Asp Ala Met
            20                  25                  30

Gly Arg Val Arg Arg Gln Tyr Cys Val Pro Val Asp Gln Pro Cys Ser
        35                  40                  45

Leu Asn Thr Gln Pro Cys Cys Asp Asp Ala Thr Cys Thr Gln Glu Leu
    50                  55                  60

Asn Glu Asn Asp Asn Thr Val Tyr Tyr Cys Arg Ala
65                  70                  75

<210> SEQ ID NO 27
<211> LENGTH: 39
<212> TYPE: PRT
<213> ORGANISM: Atrax robustus

<400> SEQUENCE: 27

Gln Tyr Cys Val Pro Val Asp Gln Pro Cys Ser Leu Asn Thr Gln Pro
1               5                   10                  15

Cys Cys Asp Asp Ala Thr Cys Thr Gln Glu Leu Asn Glu Asn Asp Asn
            20                  25                  30

Thr Val Tyr Tyr Cys Arg Ala
        35

<210> SEQ ID NO 28
<211> LENGTH: 228
<212> TYPE: DNA
<213> ORGANISM: Atrax robustus

<400> SEQUENCE: 28
atgaataccg caacaggttt catcgtcctt ttggttttgg cgacagttct cggaggtatt     60
gaagctagag aatctcatat gagaaaagat gccatgggaa gagttcgtcg acaatattgc    120
gttccagttg atcaaccgtg ctctctgaat acccaaccgt gctgcgatga tgccacgtgc    180
acacaagagc taaatgaaaa cgacaacact gtttattatt gcagggct                 228

<210> SEQ ID NO 29
<211> LENGTH: 25
<212> TYPE: DNA
<213> ORGANISM: Hadronyche versuta

<400> SEQUENCE: 29
cacccctaat acgactcact atagg                                           25

<210> SEQ ID NO 30
<211> LENGTH: 24
<212> TYPE: DNA
<213> ORGANISM: Hadronyche versuta
<220> FEATURE:
<221> NAME/KEY: misc_feature
<222> LOCATION: (4)..(4)
<223> OTHER INFORMATION: n is a, g, c or t

<400> SEQUENCE: 30
rttnccrtty tcrttytcyt craa                                            24

<210> SEQ ID NO 31
<211> LENGTH: 20
<212> TYPE: DNA
<213> ORGANISM: Hadronyche versuta

<400> SEQUENCE: 31
tgctgcaata tgaataccgc 20

<210> SEQ ID NO 32
<211> LENGTH: 24
<212> TYPE: DNA
<213> ORGANISM: Hadronyche versuta

<400> SEQUENCE: 32
gggcaggttt tttttttttt tttt 24

<210> SEQ ID NO 33
<211> LENGTH: 42
<212> TYPE: DNA
<213> ORGANISM: Hadronyche versuta

<400> SEQUENCE: 33
tgcgttccgg ttgaccagcc gtgctccctg aacacccagc cg 42

<210> SEQ ID NO 34
<211> LENGTH: 57
<212> TYPE: DNA
<213> ORGANISM: Hadronyche versuta

<400> SEQUENCE: 34
cgttacgctc ctgggtgcag gtagcgtcgt cgcagcacgg ctgggtgttc agggagc 57

<210> SEQ ID NO 35
<211> LENGTH: 54
<212> TYPE: DNA
<213> ORGANISM: Hadronyche versuta

<400> SEQUENCE: 35
cgctacctgc acccaggagc gtaacgaaaa cggtcacacc gtttactact gccg 54

<210> SEQ ID NO 36
<211> LENGTH: 29
<212> TYPE: DNA
<213> ORGANISM: Hadronyche versuta

<400> SEQUENCE: 36
gaattctcaa gcacggcagt agtaaacgg 29

<210> SEQ ID NO 37
<211> LENGTH: 29
<212> TYPE: DNA
<213> ORGANISM: Hadronyche versuta

<400> SEQUENCE: 37
cgggatcctg cgttccggtt gaccagccg 29

<210> SEQ ID NO 38
<211> LENGTH: 22
<212> TYPE: PRT
<213> ORGANISM: Hadronyche versuta
<220> FEATURE:
<221> NAME/KEY: X
<222> LOCATION: (4)..(4)
<223> OTHER INFORMATION: A or T -continued

```
<220> FEATURE:
<221> NAME/KEY: X
<222> LOCATION: (10)..(10)
<223> OTHER INFORMATION: L or F
<220> FEATURE:
<221> NAME/KEY: X
<222> LOCATION: (16)..(16)
<223> OTHER INFORMATION: I or V
<220> FEATURE:
<221> NAME/KEY: X
<222> LOCATION: (20)..(20)
<223> OTHER INFORMATION: I or V

<400> SEQUENCE: 38

Met Asn Thr Xaa Thr Gly Phe Ile Val Xaa Leu Val Leu Ala Thr Xaa
1               5                   10                  15

Leu Gly Gly Xaa Glu Ala
            20


<210> SEQ ID NO 39
<211> LENGTH: 15
<212> TYPE: PRT
<213> ORGANISM: Hadronyche versuta
<220> FEATURE:
<221> NAME/KEY: X
<222> LOCATION: (1)..(1)
<223> OTHER INFORMATION: G or R or or other sequences covalently
      attached upstream of a mature U-ACTX polypeptide

<400> SEQUENCE: 39

Xaa Glu Ser His Met Arg Lys Asp Ala Met Gly Arg Val Arg Arg
1               5                   10                  15
```

INSECTICIDAL POLYPEPTIDES AND METHODS OF USE THEREOF

CROSS REFERENCE TO RELATED APPLICATIONS

This application claims the benefit of and is a divisional application and claims priority under 35 U.S. §119(e) to U.S. Provisional Application No. 60/625,297 filed on Nov. 4, 2004, and to U.S. patent application Ser. No. 11/267,815, filed on Nov. 4, 2005, now U.S. Pat. No. 7,354,993, and to U.S. patent application Ser. No. 12/074,950, filed on Mar. 7, 2008, now U.S. Pat. No. 7,880,060, each of which is incorporated herein by reference in its entirety.

STATEMENT REGARDING FEDERALLY SPONSORED RESEARCH & DEVELOPMENT

The U.S. Government has certain rights in this invention pursuant to National Science Foundation Grant No. MCB0234638.

BACKGROUND

Although only a small minority of insects are classified as pests, they nevertheless destroy around 20% of the world's food supply and transmit a diverse array of human and animal pathogens. Control of insect pests is therefore an issue of worldwide agronomic and medical importance. Arthropod pests such as insects have been controlled primarily with chemical insecticides ever since the introduction of DDT in the 1940s. However, control of insect pests in the United States and elsewhere in the world is becoming increasingly complicated for several reasons. First, chemical control subjects the insect population to Darwinian selection and, as a consequence, more than 500 species of arthropods have developed resistance to one or more classes of chemical insecticides. Second, growing awareness of the undesirable environmental and ecological consequences of chemical insecticides, such as toxicity to non-target organisms, has led to revised government regulations that place greater demands on insecticide risk assessment. The loss of entire classes of insecticides due to resistance development or de-registration, combined with more demanding registration requirements for new insecticides, is likely to decrease the pool of effective chemical insecticides in the near future.

Over the past decade, a number of "environmentally friendly" bioinsecticide strategies have been proposed to combat highly resistant insect pests. One recently introduced, and thus far highly successful, approach is the production of transgenic crops that express insecticidal toxins, such as engineered potato, corn, and cotton crops that express delta-endotoxins from the soil bacterium *Bacillus thuringiensis*. An alternative bioinsecticide strategy that has been successfully field-trialled, and which obviates the problem of introducing a foreign protein into the food supply, is the release of insect-specific viruses that have been engineered to express insecticidal peptide neurotoxins.

A number of investigators have recognized spider venoms as a possible source of insect-specific toxins for agricultural applications. A class of peptide toxins known as the omega-atracotoxins are disclosed in U.S. Pat. No. 5,763,568 as being isolated from Australian funnel-web spiders by screening the venom for "anti-cotton bollworm" activity. One of these compounds, designated omega-ACTX-Hv1a, has been shown to selectively inhibit insect, as opposed to mammalian, voltage-gated calcium channel currents. A second, unrelated family of insect-specific peptidic calcium channel blockers are disclosed as being isolated from the same family of spiders in U.S. Pat. No. 6,583,264.

While several insecticidal peptide toxins isolated from scorpions and spiders appear to be promising leads for the development of insecticides, there still remains a significant need for compounds that act quickly and with high potency against insects, but which display a differential toxicity between insects and vertebrates.

SUMMARY

In one embodiment, a purified polypeptide comprises any one of SEQ ID NOs. 2, 6, 9, 12, 15, 18, and 27. In another embodiment, a purified polypeptide comprises an amino acid sequence that is greater than or equal to about 70% identical to SEQ ID NO: 2, wherein the polypeptide has insecticidal activity.

In still another embodiment, an insecticidal composition comprises an insecticidally effective amount of the foregoing purified polypeptides an agriculturally acceptable carrier.

In another embodiment, an isolated polynucleotide encodes a polypeptide comprising any one of SEQ ID NOs 2 6, 9, 12, 15, 18, 21, 24 and 27. In yet another embodiment, an isolated polynucleotide encodes a polypeptide comprising an amino acid sequence have greater than or equal to about 70% identity to SEQ ID NO:2, wherein the polypeptide has insecticidal activity.

In another embodiment, an expression vector comprises a polynucleotide encoding any one of SEQ ID NOs. 2 6, 9, 12, 15, 18, 21, 24 and 27 operably linked to an expression control sequence.

In yet another embodiment, a host cell comprises an expression vector comprising a polynucleotide encoding any one of SEQ ID NOs. 2 6, 9, 12, 15, 18, 21, 24 and 27 operably linked to an expression control sequence.

In one embodiment, an insect virus comprises a polynucleotide encoding a polypeptide comprising an amino acid sequence have greater than or equal to about 70% identity to SEQ ID NO:2, wherein the polypeptide has insecticidal activity.

In one embodiment, a transgenic insect comprises a polynucleotide encoding a polypeptide comprising an amino acid sequence have greater than or equal to about 70% identity to SEQ ID NO: 2, wherein the polypeptide has insecticidal activity.

In a further embodiment, a method of treating air insect or an insect larva comprises contacting the insect or insect larva with an insecticidally effective amount of a U-ACTX polypeptide, wherein the U-ACTX polypeptide comprises an amino acid sequence that is greater than or equal to about 70% identical to SEQ ID NO:2, wherein the U-ACTX polypeptide has insecticidal activity. In one aspect, a method of treating a plant comprises contacting the plant with an insecticidally effective amount of a U-ACTX polypeptide, wherein the U-ACTX polypeptide comprises an amino acid sequence that is greater than or equal to about 70% identical to SEQ ID NO:2, wherein the U-ACTX polypeptide has insecticidal activity.

In yet another aspect, a transgenic plant is included, wherein the transgenic plant expresses a U-ACTX polypeptide, wherein the U-ACTX polypeptide comprises an amino acid sequence that is greater than or equal to about 70% identical to SEQ ID NO:2, wherein the U-ACTX polypeptide has insecticidal activity.

BRIEF DESCRIPTION OF THE DRAWINGS

FIG. 1 shows an alignment of the complete prepropolypeptide sequences of nine U-ACTX homologs.

FIG. 2 shows a method of constructing a synthetic gene for production of recombinant U-ACTX.

FIG. 3 is a dose-response curve resulting from injection of U-ACTX into houseflies.

FIG. 4 is a dose-response curve showing the effects of rU-ACTX-Hv1a on calcium currents in DUM neurons, measured as $I_{Ca}$.

FIG. 5 is a dose response curve showing the effects of U-ACTX-Hv1a on pSlo channels expressed in HEK293 cells, and measured as $I_{K(Ca)}$.

The above-described and other features will be appreciated and understood by those skilled in the art from the following detailed description, drawings, and appended claims.

DETAILED DESCRIPTION

The present invention includes the U-ACTX polypeptides, and polynucleotides encoding these polypeptides. In one embodiment, the polypeptide is a component of the venom of a spider of the genera *Atrax* or *Hadronyche*. The U-ACTX polypeptides and polynucleotides encoding them may be employed as insecticides, either alone or in combination with other insecticidal polypeptides or genes thereof. An insecticide or an insecticidal composition is one that is toxic to one or more species of insect. Insecticidal activity refers to the ability of polypeptides to kill or paralyze insects, or to inhibit the insect development or growth in such a manner that, for example in the case of agricultural applications, the insects provide less damage to a plant and plant yield is not significantly adversely affected. Polypeptides having insecticidal activity are also referred to as toxic to insects. Insecticidal specificity is the specificity of a U-ACTX polypeptide for one or more insect species. The $LD_{50}$ is the dose of a U-ACTX polypeptide that results in the death of 50% of the insects tested.

As used herein, U-ACTX or U-ACTX polypeptide includes U-ACTX-Hv1a or a homolog thereof. In one embodiment, there is provided an insecticidal polypeptide that is toxic to adult and/or larval insects, the polypeptide having a molecular mass of approximately 4,300 Daltons and a length of 38 to 39 amino acid residues. In one embodiment, the polypeptide is capable of forming three intrachain disulfide bonds. Insecticidal activity may be demonstrated by the development of uncontrolled hyperexcitability in insects injected with the U-ACTX polypeptide, eventually leading to death. U-ACTX polypeptides can cause irreversible toxicity when injected into insects such as the house fly *Musca domestica*, the house cricket *Acheta domestica*, and other insect species.

The mature U-ACTX sequences exhibit less than 50% sequence identity with previously isolated insecticidal peptide toxins such as, for example, the omega-ACTX-1 family of insecticidal toxins previously isolated from the venom of Australian funnel-web spiders. Whereas insects injected with omega-ACTX-Hv1a exhibit spastic paralysis followed by death, rU-ACTX-Hv1a induces uncontrolled hyperexcitability in injected insects which precedes paralysis and death. Thus, U-ACTX-Hv1a has a different mode of action than the previously characterized omega-ACTX-Hv1a.

The U-ACTX polypeptide may be in the form of a mature polypeptide or a prepropolypeptide. Without being held to theory, it is believed that the biologically active form of the U-ACTX polypeptide is produced by posttranslational proteolytic processing (e.g., cleavage) of the prepropolypeptide precursor to produce the mature polypeptide. Cleavage may be endoproteolytic cleavage of the prepropolypeptide by a protease that recognizes a particular amino acid sequence motif in the prepropolypeptide. The "pre" portion of the prepropolypeptide refers to the signal peptide portion of the prepropolypeptide. Without being held to theory, it is believed that the signal sequence is responsible for targeting the prepropolypeptide to, as well as its translocation across, the endoplasmic reticulum membrane in cells that produce U-ACTX. In one embodiment, the signal peptide sequence includes SEQ ID NO: 38 MNTX$_1$TGFIVX$_2$LVLATX$_3$LGGX$_4$EA, wherein X$_1$ is A or T, X$_2$ is L or F, X$_3$ is I or V, and X$_4$ is I or V. Other signal sequences that function in a similar manner may also be employed. The "pro" part of the prepropolypeptide refers to the sequence SEQ ID NO: 39 X$_5$ESHMRKDAMGRVRR, wherein X$_5$ is G or R; or other sequences covalently attached upstream of a mature U-ACTX polypeptide. Without being held to theory, possible roles for the pro sequence include facilitating toxin export from the endoplasmic reticulum, assisting enzyme-catalyzed oxidative folding of the mature toxin sequence, and signaling enzymes involved in proteolytic processing and posttranslational modification. The RR motif in the pro sequence is believed to be the endoprotease cleavage site. A purified polypeptide comprising a U-ACTX polypeptide may thus further comprise a signal peptide sequence, a pro sequence, or a combination comprising one or more of the foregoing sequences. The prepropolypeptide architecture of the U-ACTX toxins appears similar to that determined by the inventors for other toxins expressed in the venom gland of Australian funnel-web spiders.

In one embodiment, the U-ACTX polypeptide is a prepropeptide from *Hadronyche versuta* having the sequence:

```
SEQ ID NO: 1:
Met-Asn-Thr-Ala-Thr-Gly-Phe-Ile-Val-Leu-Leu-Val-

Leu-Ala-Thr-Val-Leu-Gly-Gly-Val-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Arg-Asn-Glu-Asn-Gly-His-Thr-Val-Tyr-

Tyr-Cys-Arg-Ala

(MNTATGFIVLLVLATVLGGVEAGESHMRKDAMGRVRRQYCVPVDQPC

SLNTQPCCDDATCTQERNENGHTVYYCRA)
```

The mature polypeptide formed by cleavage of the prepropolypeptide of SEQ ID NO: 1 is U-ACTX-Hv1a:

```
SEQ ID NO: 2:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Arg-Asn-Glu-Asn-Gly-His-Thr-Val-Tyr-Tyr-

Cys-Arg-Ala

(QYCVPVDQPCSLNTQPCCDDATCTQERNENGHTVYYCRA)
```

In one embodiment, the U-ACTX polypeptide is rU-ACTX-Hv1a (SEQ ID NO:3) as defined herein:

SEQ ID NO: 3:
Gly-Ser-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Arg-Asn-Glu-Asn-Gly-His-Thr-Val-Tyr-Tyr-

Cys-Arg-Ala (GSCVPVDQPCSLNTQPCCDDATCTQERNENGHTVYYCRA)

rU-ACTX-HV1a (SEQ ID NO:3) is a recombinant version of the mature form of U-ACTX-Hv1a in which the first two residues (Gln-Tyr) of the presumed mature toxin sequence (SEQ ID NO:2) have been replaced by the dipeptide sequence Gly-Ser.

A polynucleotide encoding SEQ ID NO:2 is

SEQ ID NO: 4:
ATGAATACCGCAACAGGTTTCATCGTCCTTTTGGTTTTGGCGACAGTTC

TAGGAGGAGTTGAAGCAGGAGAATCTCATATGAGAAAAGATGCCATGGG

AAGAGTTCGTCGACAATATTGCGTTCCAGTTGATCAACCGTGCTCCCTG

AATACCCAACCGTGCTGCGATGATGCCACGTGCACACAAGAGCGGAATG

AAAACGGCCACACTGTTTATTATTGCAGGGCT

Also included in the invention are eight homologs of U-ACTX-Hv1a which were also isolated by analysis of venom gland cDNA libraries. The prepropolypeptide sequences (SEQ ID NOs: 5, 8, 11, 14, 17, 20, 23, and 26), mature polypeptide sequences (SEQ ID NOs: 6, 9, 12, 15, 18, 21, 24 and 27) as well as the DNAs that encode them (SEQ ID NOs: 7, 10, 13, 16, 19, 22, 25, and 28) are included.

The prepropolypeptide of the first homolog from *Hadronyche versuta* is:

SEQ ID NO: 5:
Met-Asn-Thr-Ala-Thr-Gly-Phe-Ile-Val-Leu-Leu-Val-

Leu-Ala-Thr-Ile-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Arg-Asn-Glu-Asn-Gly-His-Thr-Val-Tyr-

Tyr-Cys-Arg (MNTATGFIVLLVLATILGGIEAGESHMRKDAMGRVRRQYCVPVDQPC

SLNTQPCCDDATCTQERNENGHTVYYCR)

The mature polypeptide of the first homolog from *Hadronyche versuta* is:

SEQ ID NO: 6:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Arg-Asn-Glu-Asn-Gly-His-Thr-Val-Tyr-Tyr-

Cys-Arg (QYCVPVDQPCSLNTQPCCDDATCTQERNENGHTVYYCR)

A polynucleotide encoding the mature polypeptide of the first homolog from *Hadronyche versuta* is:

SEQ ID NO: 7:
ATGAATACCGCAACAGGTTTCATCGTCCTTTTGGTTTTGGCGACAATTC

TCGGAGGTATTGAAGCAGGAGAATCTCATATGAGAAAAGATGCCATGGG

AAGAGTTCGTCGACAATATTGCGTTCCAGTTGATCAACCGTGCTCTCTG

AATACCCAACCGTGCTGCGATGATGCCACGTGCACACAAGAGCGGAATG

AAAACGGCCACACTGTTTATTATTGCAGG

The prepropolypeptide of the second homolog from *Hadronyche versuta* is:

SEQ ID NO: 8:
Met-Asn-Thr-Ala-Thr-Gly-Phe-Ile-Val-Leu-Leu-Val-

Leu-Ala-Thr-Val-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Leu-Asn-Glu-Asn-Asp-Asn-Thr-Val-Tyr-

Tyr-Cys-Arg (MNTATGFIVLLVLATVLGGIEAGESHMRKDAMGRVRRQYCVPVDQPC

SLNTQPCCDDATCTQELNENDNTVYYCR)

The mature polypeptide of the second homolog from *Hadronyche versuta* is:

SEQ ID NO: 9
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Asp-Asn-Thr-Val-Tyr-Tyr-

Cys-Arg (QYCVPVDQPCSLNTQPCCDDATCTQELNENDNTVYYCR)

A polynucleotide encoding the mature polypeptide of the second homolog from *Hadronyche versuta* is:

SEQ ID NO: 10:
ATGAATACCGCAACAGGTTTCATCGTCCTTTTGGTTTTGGCGACAGTTC

TCGGAGGTATTGAAGCAGGAGAATCTCATATGAGAAAAGATGCCATGGG

AAGAGTTCGTCGACAATATTGCGTTCCAGTTGATCAACCGTGCTCTCTG

AATACCCAACCGTGCTGCGATGATGCCACGTGCACACAAGAACTAAATG

AAAACGACAACACTGTTTATTATTGCAGG

The prepropolypeptide of the third homolog from *Hadronyche versuta* is:

SEQ ID NO: 11:
Met-Asn-Thr-Ala-Thr-Gly-Phe-Ile-Val-Leu-Leu-Val-

Leu-Ala-Thr-Ile-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

-continued

Thr-Gln-Glu-Arg-Asn-Glu-Asn-Gly-His-Thr-Val-Tyr-

Tyr-Cys-Arg-Ala (MNTATGFIVLLVLATILGGIEAGESHMRKDAMGRVRRQYCVPVDQPC

SLNTQPCCDDATCTQERNENGHTVYYCRA)

The mature polypeptide of the third homolog from *Hadronyche versuta* is:

SEQ ID NO: 12:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Arg-Asn-Glu-Asn-Gly-His-Thr-Val-Tyr-Tyr-

Cys-Arg-Ala (QYCVPVDQPCSLNTQPCCDDATCTQERNENGHTVYYCRA)

A polynucleotide encoding the mature polypeptide of the third homolog from *Hadronyche versuta* is:

SEQ ID NO: 13:
ATGAATACCGCAACAGGTTTCATCGTCCTTTTGGTTTTGGCGACAATTC

TCGGAGGTATTGAAGCAGGAGAATCTCATATGAGAAAAGACGCCATGGG

AAGAGTTCGTCGACAATATTGCGTTCCAGTTGATCAACCGTGCTCTCTG

AATACCCAACCGTGCTGCGATGATGCCACGTGCACACAAGAGCGGAATG

AAAACGGCCACACTGTTTATTATTGCAGGGCT

The prepropolypeptide of the fourth homolog from *Hadronyche versuta* is:

SEQ ID NO: 14:
Met-Asn-Thr-Ala-Thr-Gly-Phe-Ile-Val-Leu-Leu-Val-

Leu-Ala-Thr-Val-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Leu-Asn-Glu-Asn-Ala-Asn-Pro-Val-Tyr-

Tyr-Cys-Arg-Ala (MNTATGFIVLLVLATVLGGIEAGESHMRKDAMGRVRRQYCVPVDQPC

SLNTQPCCDDATCTQELNENANPVYYCRA)

The mature polypeptide of the fourth homolog from *Hadronyche versuta* is:

SEQ ID NO: 15:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Ala-Asn-Pro-Val-Tyr-Tyr-

Cys-Arg-Ala (QYCVPVDQPCSLNTQPCCDDATCTQELNENANPVYYCRA)

A polynucleotide encoding the mature polypeptide of the fourth homolog from *Hadronyche versuta* is:

SEQ ID NO: 16:
ATGAATACCGCAACAGGTTTCATCGTCCTTTTGGTTTTGGCGACAGTTC

TCGGAGGTATTGAAGCAGGAGAATCTCATATGAGAAAAGATGCCATGGG

AAGAGTTCGTCGCCAATATTACGTTCCAGTTGATCAACCGTGCTCTTTG

AATACCCAACCGTGCTGCGATGATGCCACGTGCACCCAAGAGCTAAATG

AAAACGCCAACCCTGTTTATTATTGCAGGGCT

The prepropolypeptide of the fifth homolog from *Hadronyche versuta* is:

SEQ ID NO: 17:
Met-Asn-Thr-Thr-Thr-Gly-Phe-Ile-Val-Leu-Leu-Val-

Leu-Ala-Thr-Ile-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Leu-Asn-Glu-Asn-Asp-Asn-Thr-Val-Tyr-

Tyr-Cys-Arg-Ala (MNTTTGFIVLLVLATILGGIEAGESHMRKDAMGRVRRQYCVPVDQPCSL
NTQPCCDDATCTQELNENDNTVYYCRA)

The mature polypeptide of the fifth homolog from *Hadronyche versuta* is:

SEQ ID NO: 18:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Asp-Asn-Thr-Val-Tyr-Tyr-

Cys-Arg-Ala (QYCVPVDQPCSLNTQPCCDDATCTQELNENDNTVYYCRA)

A polynucleotide encoding the mature polypeptide of the fifth homolog from *Hadronyche versuta* is:

SEQ ID NO: 19:
ATGAATACCACAACAGGTTTCATCGTCCTTTTGGTTTTGGCGACAATTCT

CGGAGGTATTGAAGCAGGAGAATCTCATATGAGAAAAGATGCCATGGGAA

GAGTTCGTCGACAATATTGCGTTCCAGTTGATCAACCGTGCTCTCTGAAT

ACCCAACCGTGCTGCGATGATGCCACGTGCACACAAGAGCTAAATGAAAA

CGACAACACTGTTTATTATTGCAGGGCT

The prepropolypeptide of the sixth homolog from *Hadronyche versuta* is:

SEQ ID NO: 20:
Met-Asn-Thr-Ala-Thr-Gly-Phe-Ile-Val-Leu-Leu-Val-

Leu-Ala-Thr-Val-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

-continued

Thr-Gln-Glu-Leu-Asn-Glu-Asn-Asp-Asn-Thr-Val-Tyr-

Tyr-Cys-Arg-Ala (MNTATGFIVLLVLATVLGGIEAGESHMRKDAMGRVRRQYCVPVDQPCSLNTQPCCDDATCTQELNENDNTVYYCRA)

The mature polypeptide of the sixth homolog from *Hadronyche versuta* is:

SEQ ID NO: 21
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Asp-Asn-Thr-Val-Tyr-Tyr-

Cys-Arg-Ala (QYCVPVDQPCSLNTQPCCDDATCTQELNENDNTVYYCRA)

A polynucleotide encoding the mature polypeptide of the sixth homolog from *Hadronyche versuta* is:

SEQ ID NO: 22
ATGAATACCGCAACAGGTTTCATCGTCCTTTTGGTTTTGGCGACAGTTCT

CGGAGGTATTGAAGCAGGAGAATCTCATATGAGAAAAGATGCCATGGGAA

GAGTTCGTCGACAATATTGCGTTCCAGTTGATCAACCGTGCTCTCTGAAT

ACCCAACCGTGCTGCGATGATGCCACGTGCACACAAGAACTAAATGAAAA

CGACAACACTGTTTATTATTGCAGGGCT

The prepropolypeptide of the seventh homolog from *Hadronyche versuta* is:

SEQ ID NO: 23:
Met-Asn-Thr-Ala-Thr-Gly-Phe-Ile-Val-Phe-Leu-Val-

Leu-Ala-Thr-Val-Leu-Gly-Gly-Ile-Glu-Ala-Gly-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Leu-Asn-Glu-Asn-Asp-Asn-Thr-Val-Tyr-

Tyr-Cys-Arg-Ala (MNTATGFIVFLVLATVLGGIEAGESHMRKDAMGRVRRQYCVPVDQPCSLNTQPCCDDATCTQELNENDNTVYYCRA)

The mature polypeptide of the seventh homolog from *Hadronyche versuta* is:

SEQ ID NO: 24:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Asp-Asn-Thr-Val-Tyr-Tyr-

Cys-Arg-Ala (QYCVPVDQPCSLNTQPCCDDATCTQELNENDNTVYYCRA)

A polynucleotide encoding the mature polypeptide of the seventh homolog from *Hadronyche versuta* is:

SEQ ID NO: 25:
ATGAATACCGCAACAGGTTTCATCGTCTTTTTGGTTTTGGCGACAGTTCT

CGGAGGTATTGAAGCAGGAGAATCTCATATGAGAAAAGATGCCATGGGAA

GAGTTCGTCGACAATATTGCGTTCCAGTTGATCAACCGTGCTCTCTGAAT

ACCCAACCGTGCTGCGATGATGCCACGTGCACACAAGAACTAAATGAAAA

CGACAACACTGTTTATTATTGCAGGGCT

The prepropolypeptide of the eighth homolog from *Atrax robustus* is:

SEQ ID NO: 26:
Met-Asn-Thr-Ala-Thr-Gly-Phe-Ile-Val-Leu-Leu-Val-

Leu-Ala-Thr-Val-Leu-Gly-Gly-Ile-Glu-Ala-Arg-Glu-

Ser-His-Met-Arg-Lys-Asp-Ala-Met-Gly-Arg-Val-Arg-

Arg-Gln-Tyr-Cys-Val-Pro-Val-Asp-Gln-Pro-Cys-Ser-

Leu-Asn-Thr-Gln-Pro-Cys-Cys-Asp-Asp-Ala-Thr-Cys-

Thr-Gln-Glu-Leu-Asn-Glu-Asn-Asp-Asn-Thr-Val-Tyr-

Tyr-Cys-Arg-Ala (MNTATGFIVLLVLATVLGGIEARESHMRKDAMGRVRRQYCVPVDQPCSLNTQPCCDDATCTQELNENDNTVYYCRA)

The mature polypeptide of the eighth homolog from *Atrax robustus* is:

SEQ ID NO: 27:
Gln-Tyr-Cys-Val-Pro-Val-Asp-Gln-Pro-Cys-Ser-Leu-

Asn-Thr-Gln-Pro-Cys-Cys-Asp-Asp-Ala-Thr-Cys-Thr-

Gln-Glu-Leu-Asn-Glu-Asn-Asp-Asn-Thr-Val-Tyr-Tyr-

Cys-Arg-Ala (QYCVPVDQPCSLNTQPCCDDATCTQELNENDNTVYYCRA)

A polynucleotide encoding the eighth homolog from *Atrax robustus* is:

SEQ ID NO: 28:
ATGAATACCGCAACAGGTTTCATCGTCCTTTTGGTTTTGGCGACAGTTCT

CGGAGGTATTGAAGCTAGAGAATCTCATATGAGAAAAGATGCCATGGGAA

GAGTTCGTCGACAATATTGCGTTCCAGTTGATCAACCGTGCTCTCTGAAT

ACCCAACCGTGCTGCGATGATGCCACGTGCACACAAGAGCTAAATGAAAA

CGACAACACTGTTTATTATTGCAGGGCT

The invention includes isolated or purified U-ACTX polypeptides. An "isolated" or "purified" polypeptide or fragment thereof is substantially free of cellular material or other contaminating polypeptides from the cell, tissue source or venom from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Thus, a polypeptide that is substantially free of cellular material includes preparations of polypeptide having less than about 30%, about 20%, about 10%, or about 5% (by dry weight) of heterologous polypeptide (also referred to herein as a "contaminating polypeptide"). In one embodiment, the preparation is at least about 75% by weight pure, more specifically at least about 90% by weight pure, and most specifically at least about 95% by weight pure. A substantially pure U-ACTX polypeptide may be obtained, for example, by extraction from a natural source (e.g., an insect cell); by expression of a recombinant nucleic acid encoding a U-ACTX polypeptide; or by chemically synthesizing the polypeptide. Purity can be measured by any appropriate method, e.g., by column chromatography, polyacrylamide gel electrophoresis, mass spectrometry, or by high pressure liquid chromatography (HPLC) analysis.

The invention also includes homologs of U-ACTX. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog", meaning a polynucleotide or polypeptide that is the functional equivalent of a polynucleotide or polypeptide in another species, and "paralog" meaning a functionally similar sequence when considered within the same species. Paralogs present in the same species or orthologs of U-ACTX genes in other species can readily be identified without undue experimentation, by molecular biological techniques well known in the art.

As used herein, "percent homology" of two amino acid sequences or of two nucleic acids is determined using the algorithm of Karlin and Altschul (1990) *Proc. Natl. Acad. Sci.*, U.S.A. 87, 2264-2268. Such an algorithm is incorporated into the NBLAST and XBLAST programs of Altschul et al. (1990) *J Mol. Biol.* 215, 403-410. BLAST nucleotide searches are performed with the NBLAST program, score=100, wordlength 12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:2). To obtain gapped alignments for comparison purposes, Gapped BLAST is utilized as described in Altschul et al. (1997) *Nucleic Acids Res.* 25, 3389-3402. When utilizing BLAST and Gapped BLAST programs, the default parameters are typically used.

Related polypeptides are aligned with U-ACTX by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. Mature U-ACTX and homologous polypeptides are preferably greater than or equal to about 70%, specifically greater than or equal to about 80%, more specifically greater than or equal to about 90%, and most specifically greater than or equal to about 95% identical. SEQ ID NO:2 may be employed as a reference polypeptide.

Where a particular polypeptide is said to have a specific percent identity to a reference polypeptide of a defined length, the percent identity is relative to the reference peptide. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

By "modification" of the primary amino acid sequence it is meant to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a polypeptide consisting of a primary amino acid sequence which is identical to a portion of the primary sequence of the specified polypeptide). By "modification" it is also meant to include polypeptides that are altered as a result of post-translational events which change, for example, the glycosylation, amidation (e.g., C-terminal amidation), lipidation pattern, or the primary, secondary, or tertiary structure of the polypeptide. N-terminal and/or C-terminal modifications are possible.

Reference herein to either the nucleotide or amino acid sequence of U-ACTX also includes reference to naturally occurring variants of these sequences. Nonnaturally occurring variants that differ from SEQ ID NOs: 1, 5, 8, 11, 14, 17, 20, 23, and 26 for the prepropolypeptide and SEQ ID NOs: 2, 6, 9, 12, 15, 18, 21, 24, and 27 for the mature polypeptide, and retain biological function, are also included herein. The variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cystine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the insecticidal activity of the U-ACTX polypeptide derivatives.

Reference to U-ACTX also refers to polypeptide derivatives of U-ACTX. As used herein, "polypeptide derivatives" include those polypeptides differing in length from a naturally-occurring U-ACTX and comprising about fifteen or more amino acids in the same primary order as is found in U-ACTX. Polypeptide derivatives can be longer than U-ACTX, shorter than U-ACTX (e.g., active fragments), so long as the polypeptide derivatives have insecticidal activity. Polypeptides having substantially the same amino acid sequence as U-ACTX but possessing minor amino acid substitutions that do not substantially affect the insecticidal activity of U-ACTX polypeptide derivatives, are within the definition of U-ACTX polypeptide derivatives.

Homologs of U-ACTX can be identified in several ways. In one method, native mRNA sequences encoding the precursors of U-ACTX orthologs can be identified by using standard molecular biology techniques to screen spider venom-gland cDNA libraries for such orthologs. The amino acid sequence of the mature U-ACTX ortholog can be obtained from translation of the identified cDNA sequences by noting that endoproteolytic cleavage of the propeptide to give the mature toxin most likely occurs on the C-terminal side of an Arg-Arg processing site that immediately precedes the mature toxin (see second arrow in FIG. 1). Native mature U-ACTX ortholog can then be isolated by chromatographic fractionation of the venom, followed by identification and purification of a peptide toxin with a mass matching that predicted from the U-ACTX ortholog cDNA sequence. In another method, synthetic mature toxin can be produced by solid-phase peptide synthesis of the U-ACTX sequence followed by cysteine oxidation to form the native disulfide isomer as described previously for production of synthetic J-atracotoxin-Hv1c (Wang et al. (2000) *Nature Structural Biology* 7, 505-513). A U-ACTX polypeptide may be oxidized and folded into its native three-dimensional structure by incubating the reduced, lyophilized peptide in a glutathione redox buffer. A suitable glutathione redox buffer includes 200 mM 3-[N-morpholino]propanesulphonic acid (MOPS) pH 7.3, 400 mM KCl, 2 mM EDTA, 4 mM reduced glutathione (GSH) and 2 mM oxidized glutathione (GSSG), although numerous variants are well known to those practiced in the art. This reaction mixture is incubated overnight at 4° C., room temperature, or 37° C., for example, and then fractionated using reverse-phase HPLC to separate individual disulfide isomers. Fractions may be collected and assayed for insecticidal activity. In yet another method, the U-ACTX ortholog can be synthesized, chemically or by recombinant DNA techniques, from cDNA encoding the U-ACTX ortholog. In another method, the U-ACTX ortholog can be prepared using recombinant DNA techniques by constructing a synthetic gene encoding the U-ACTX sequence by methods known in the art.

The invention includes isolated U-ACTX polynucleotides such as, for example, SEQ ID NOs: 4, 7, 10, 13, 16, 19, 22, 25, and 28. The term "isolated polynucleotide" includes polynucleotides that are separated from other nucleic acid molecules present in the natural source of the nucleic acid. For example, with regard to genomic DNA, the term "isolated" includes polynucleotides that are separated from the chromosome with which the genomic DNA is naturally associated. An "isolated" polynucleotide is free of sequences that naturally flank the nucleic acid (i.e., sequences located at the 5' and/or 3' ends of the nucleic acid) in the genomic DNA of the organism from which the nucleic acid is derived. For example, in various embodiments, the isolated polynucleotide can contain less than about 5 kb, about 4 kb, about 3 kb, about 2 kb, about 1 kb, about 0.5 kb, or about 0.1 kb of 5' and/or 3' nucleotide sequences which naturally flank the nucleic acid molecule in genomic DNA of the cell from which the nucleic acid is derived. Moreover, an "isolated" polynucleotide, such as a cDNA molecule, can be substantially free of other cellular material, or culture medium when produced by recombinant techniques, or substantially free of chemical precursors or other chemicals when chemically synthesized. By free of other cellular material, it is meant that an isolated polynucleotide is greater than or equal to about 70%, about 75%, about 80%, about 85%, about 90%, about 95%, or about 99% pure.

"Polynucleotide" or "nucleic acid" refers to a polymeric form of nucleotides at least 5 bases in length. The nucleotides can be ribonucleotides, deoxyribonucleotides, or modified forms of either nucleotide. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate. As used herein, the term "gene" means the segment of DNA involved in producing a polypeptide chain; it includes regions preceding and following the coding region (leader and trailer) as well as intervening sequences (introns) between individual coding segments (exons).

The polynucleotide can be a DNA molecule, a cDNA molecule, genomic DNA molecule, or an RNA molecule. The polynucleotide as DNA or RNA comprises a sequence wherein T can also be U. The polynucleotide can be complementary to a polynucleotide encoding a U-ACTX polypeptide (e.g., SEQ ID NOs: 7, 10, 13, 16, 19, 22, 25 and 28), wherein complementary refers to the capacity for precise pairing between two nucleotides. For example, if a nucleotide at a certain position of a polynucleotide is capable of hydrogen bonding with a nucleotide at the same position in a DNA or RNA molecule, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means hydrogen bonding, which may be Watson-Crick, Hoogsteen or reversed Hoogsteen hydrogen bonding, between complementary nucleoside or nucleotide bases.

In addition, polynucleotides that are substantially identical to a polynucleotide encoding a U-ACTX polypeptide (e.g., SEQ ID NOs: 7, 10, 13, 16, 19, 21, 25 and 28) or which encode proteins substantially identical to SEQ ID NO:2 are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically about 110 nucleotides.

Typically, homologous sequences can be confirmed by hybridization, wherein hybridization under stringent conditions as described, for example, in Sambrook et al., MOLECULAR CLONING: A LABORATORY MANUAL, 2nd ed. (Cold Spring Harbor Press, Cold Spring Harbor, N.Y.) is preferred. Using the stringent hybridization outlined in Sambrook et al. (i.e., washing the nucleic acid fragments twice where each wash is at room temperature for 30 minutes with 2× sodium chloride and sodium citrate (SCC) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

A homologous polypeptide may be produced, for example, by conventional site-directed mutagenesis of polynucleotides (which is one avenue for routinely identifying residues of the molecule that are functionally important or not), by random mutation, by chemical synthesis, or by chemical or enzymatic cleavage of the polypeptides.

Polynucleotides encoding U-ACTX sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding a U-ACTX polypeptide. A nucleic acid sequence employed for hybridization studies may be greater than or equal to about 14 nucleotides in length to ensure that the fragment is of sufficient length to form a stable and selective duplex molecule. Such fragments may be prepared by, for example, directly synthesizing the fragment by chemical means, by application of nucleic acid reproduction technology, such as PCR technology, or by excising selected nucleic acid fragments from recombinant plasmids containing appropriate inserts and suitable restriction sites.

The U-ACTX and homolog polynucleotides can be inserted into a recombinant expression vector or vectors. The term “recombinant expression vector” refers to a plasmid, virus, or other means known in the art that has been manipulated by insertion or incorporation of the U-ACTX genetic sequence. The term “plasmids” generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The U-ACTX polynucleotides can be inserted into a vector adapted for expression in a bacterial, plant, yeast, insect, amphibian, or mammalian cell that further comprises the regulatory elements necessary for expression of the nucleic acid molecule in the bacterial, yeast, insect, amphibian, plant or mammalian cell operatively linked to the nucleic acid molecule encoding U-ACTX. “Operatively linked” refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term “expression control sequences” refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term “control sequences” is intended to include, at a minimum, components whose presence can influence expression, and can also include additional components whose presence is advantageous, for example, leader sequences and fusion partner sequences. Expression control sequences can include a promoter. By “promoter” is meant a minimal sequence sufficient to direct transcription. Also included are those promoter elements that are sufficient to render promoter-dependent gene expression controllable for cell-type specific induction, tissue-specific induction, or promoters that are inducible by external signals or agents; such elements may be located in the 5' or 3' regions of the gene. Both constitutive and inducible promoters are included.

If an expression vector is used to transform a plant, a promoter may be selected that has the ability to drive expression in the plant. Promoters that function in plants are well known in the art. Exemplary tissue-specific plant promoters are corn sucrose synthase-1 promoter, cauliflower mosaic virus (CaMV 35S) promoter, S-E9 small subunit RuBP carboxylase promoter, and corn heat shock protein promoter.

The choice of which expression vector, and ultimately to which promoter a polypeptide coding region is operatively linked, depends directly on the functional properties desired, for example, the location and timing of protein expression and the host cell to be transformed. In one embodiment, the vector used to express the polypeptide includes a selection marker that is effective in a plant cell. Transformation vectors used to transform plants and methods of making those vectors are described, for example, in U.S. Pat. Nos. 4,971,908, 4,940,835, 4,769,061 and 4,757,011.

The expression systems may also contain signal peptide and propolypeptide sequences that facilitate expression of the toxin gene and/or folding of the toxin. These could be the native U-ACTX signal and propeptide sequences disclosed herein or other signal and/or propeptide sequences that serve the same purpose.

Insect viruses are naturally occurring insect pathogens. Insects that are susceptible to viral infection can be a target for insect viruses. They may be DNA viruses or RNA viruses. Many insect viruses and their host range are known in the art, including viruses that are host-specific and environmentally safe. The insecticidal efficacy of an insect virus can be enhanced by incorporation of a gene encoding an insect toxin into its genome, using method similar to those disclosed in U.S. Pat. No. 6,096,304. A suitable insect virus is a DNA virus that has been traditionally used as a biological control agent on insect pests, such as baculovirus (nucleopolyhedrovirus and granulovirus), and entomopoxvirus. Another example of a suitable DNA virus is the mosquito-specific baculovirus disclosed in U.S. Pat. No. 6,521,454. Suitable RNA viruses include, but are not limited to, cypovirus.

Vectors useful for expression of genes in higher plants are well known in the art and include vectors derived from the tumor-inducing (Ti) plasmid of *Agrobacterium tumefaciens* and pCaMVCN transfer control vector (available from Pharmacia, Piscataway, N.J.).

Transformation of a host cell with an expression vector or other DNA may be carried out by techniques well known to those skilled in the art. By “transformation” is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By “transformed cell” or “host cell” is meant a cell (e.g., prokaryotic or eukaryotic) into which (or into an ancestor of which) has been introduced, by means of recombinant DNA techniques, a DNA molecule encoding a polypeptide of the invention (i.e., a U-ACTX polypeptide), or fragment thereof.

When the host is a eukaryote, methods of transfection with DNA such as calcium phosphate co-precipitates, mechanical procedures such as microinjection, electroporation, insertion of a plasmid encased in liposomes, or virus vectors, as well as others known in the art, may be used. When the host is a plant cell, other means of gene introduction into the cell may also be employed such as, for example, polyethyleneglycol-mediated transformation of protoplasts, desiccation/inhibition-mediated DNA uptake, agitation with silicon carbide fibers, acceleration of DNA coated particles, injection into reproductive organs, and injection into immature embryos.

Eukaryotic cells can also be cotransfected with DNA sequences encoding a polypeptide of this disclosure, and a second foreign DNA molecule encoding a selectable phenotype, such as the herpes simplex thymidine kinase gene. Suitable markers include, for example, neomycin and hygromycin, and the like, that can be taken up by mammalian cells. Resistance to the marker can be conferred by the neomycin gene or the hygromycin gene, for example, when the gene has a suitable eukaryotic promoter. Another method is to use a eukaryotic viral vector, such as simian virus 40 (SV40), adenovirus, or bovine papilloma virus, to transiently infect or transform eukaryotic cells and express the protein. (*Eukaryotic Viral Vectors*, Cold Spring Harbor Laboratory, Gluzman ed., 1982). In one embodiment, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome will result in a recombinant virus that is viable and capable of expressing the U-ACTX polypeptide in infected hosts (e.g., Logan & Shenk (1984) *Proc. Natl. Acad. Sci. U.S.A.* 81, 3655-3659).

For long-term, high-yield production of recombinant polypeptides, stable expression is preferred. Rather than using expression vectors that contain viral origins of replication, host cells can be transformed with the cDNA encoding a U-ACTX fusion polypeptide controlled by appropriate expression control elements (e.g., promoter sequences, enhancer sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then switched to a selective media. A number of selection systems may be used, including but not limited to the herpes simplex virus thymidine kinase (Wigler et al. (1977) *Cell* 11, 223-32), hypoxanthine-guanine phosphoribosyltransferase (Szybalska & Szybalski (1962) *Proc. Natl. Acad. Sci. U.S.A.* 48, 2026-2034), and adenine phosphoribosyltransferase (Lowy et al. (1980) *Cell* 22, 817-823).

The U-ACTX polypeptides can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

U-ACTX proteins, polypeptides, or polypeptide derivatives can be purified by methods known in the art. These methods include, but are not limited to, size exclusion chromatography, ammonium sulfate fractionation, ion exchange chromatography, affinity chromatography, crystallization, electrofocusing, preparative gel electrophoresis, and combinations comprising one or more of the foregoing methods. Purification may be performed according to methods known to those of skill in the art that will result in a preparation of U-ACTX substantially free from other polypeptides and from carbohydrates, lipids, or subcellular organelles. Purity may be assessed by means known in the art, such as SDS-polyacrylamide gel electrophoresis.

A U-ACTX fusion polypeptide is also provided, comprising a U-ACTX polypeptide covalently joined to a polypeptide to which it would not be joined in nature. Fusion polypeptides are useful for use in various assay systems. Fusion polypeptides may be used, for example, to detect U-ACTX expression. For example, U-ACTX fusion polypeptides can be used to identify proteins that interact with the U-ACTX protein and influence its function. This interaction may impart specificity to the ability of U-ACTX to regulate other proteins, or it may increase or decrease the effect of U-ACTX function. Physical methods, such as protein affinity chromatography, or library-based assays for protein-protein interactions, such as the yeast two-hybrid, bacterial two-hybrid, or phage display systems, can be used for this purpose. Such methods are well known in the art.

A fusion polypeptide comprises at least two heterologous polypeptide segments fused together by means of a peptide bond. The first polypeptide segment can comprise in whole or in part the contiguous amino acids of a U-ACTX polypeptide. Where in part, at least about 8 contiguous amino acids of U-ACTX polypeptide is used, specifically at least about 10, more specifically about 15, and most specifically about 20. The first polypeptide segment can also be a full-length U-ACTX protein. The second polypeptide segment can comprise an enzyme which will generate a detectable product, such as beta-galactosidase or other enzymes that are known in the art. Alternatively, the second polypeptide segment can include a fluorescent protein such as green fluorescent protein, HcRed (Clontech) or other fluorescent proteins known in the art. Additionally, the fusion protein can be labeled with a detectable marker, such as a radioactive maker, a fluorescent marker, a chemiluminescent marker, a biotinylated marker, and the like.

Techniques for making fusion polypeptides, either recombinantly or by covalently linking two polypeptide segments are well known. Recombinant DNA methods can be used to construct U-ACTX fusion polypeptides, for example, by making a DNA construct that comprises U-ACTX coding sequence in proper reading frame with nucleotides encoding the second polypeptide segment and expressing the DNA construct in a host cell. The DNA construct can be operably linked to sequences that facilitate protein production (i.e., promoters, etc.).

In addition to fusion polypeptides, U-ACTX can be labeled in vitro by methods known in the art. U-ACTX can be conjugated to such dyes as Texas Red, rhodamine dyes, fluorescein and other dyes known in the art. Conjugation chemistries include succinimidyl ester, isothiocyanates, and maleimides. Detailed information about conjugatable dyes and conjugation chemistries can be found in the Molecular Probes Handbook of Fluorescent Probes and Research Products (Invitrogen, Carlsbad, Calif.). Such fusion polypeptides can be used for the production of antibodies that may have greater specificity and sensitivity than those generated against short amino acid sequences. In addition, fusion polypeptides may be used to examine their ability to influence cell survival, proliferation and differentiation in tissue culture assays.

Transgenic plants may be constructed that express U-ACTX polypeptide or the prepolypeptide or the prepropolypeptide form of the toxin. By "transgenic plant" it is meant a plant, or progeny thereof, derived from a "transformed plant" cell or protoplast, wherein the plant DNA (nuclear or chloroplast) contains an introduced exogenous DNA molecule not originally present in a native, non-transgenic plant of the same strain.

The development or regeneration of plants from either single plant protoplasts or various explants is well known in the art. This regeneration and growth process typically includes the selection of transformed cells, and culturing those individualized cells through the usual stages of embryonic development through the rooted plantlet stage. Transgenic embryos and seeds may be similarly regenerated. The resulting transgenic rooted shoots may be thereafter planted in an appropriate plant growth medium such as soil.

The regenerated plants may be self-pollinated to provide homozygous transgenic plants. Otherwise, pollen obtained from the regenerated plants may be crossed to seed-grown plants of agronomically important, inbred lines. Conversely, pollen from plants of those important lines may be used to pollinate regenerated plants. A transgenic plant containing a desired polypeptide may be cultivated using methods well known to one skilled in the art.

A suitable transgenic plant includes an independent segregant that can transmit the U-ACTX gene and its activity to its progeny. In one embodiment, a transgenic plant is homozygous for the U-ACTX gene; and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against one or more insects, preferably in the field, under a range of environmental conditions. The transgenic plant may be corn, soybeans, cotton, wheat, oats, barley, other grains, vegetables, fruits, fruit trees, berries, turf grass, ornamentals, shrubs and trees, and the like.

Polynucleotides encoding U-ACTX polypeptides may be employed to produce transgenic insects having particular genetic traits. Technology for the production of transgenic animals and insects are known to those of skill in the art. A polynucleotide encoding a U-ACTX polypeptide may be inserted into the insect genome using transposable elements. Integration (transposition) may be facilitated by the enzyme transposase, and the transposable element may comprise inverted repeats which function to direct the transposase to the correct position, to initiate excision. Genetic constructs, comprising a transposable element combined (in a genetic fusion) with a heterologous gene, may be prepared using conventional technology, and inserted into the insect egg to produce a transgenic insect. In addition to the U-ACTX gene, the transposable element may comprise the regulatory factors that ensure successful expression can occur.

Suitable transposable elements include, for example, Hermes from *Musca domestica*, Mariner from *D. mauritania*, piggyBAC, and Minos, found in *Drosophila hydei*. A Minos transposable element may be employed to integrate a U-ACTX polynucleotide into the genome of an insect embryo, optionally in the presence of a Minostransposase. The transposable element may be in the form of a plasmid vector together with a foreign gene and further comprising regulatory sequences, e.g. a promoter. In one embodiment, the promoter is the actin5c promoter from *D. melanogaster*. In one embodiment, the Minos transposase gene is located on a separate helper plasmid, for separate introduction into the embryo.

The transposable element may be used to integrate into the insect embryo a heterologous gene that can be expressed in vivo. Alternatively, integration of the transposable element may be employed to integrate a heterologous polynucleotide that can be used to disrupt expression of a particular gene. For example, an RNA molecule may be used for gene silencing.

The U-ACTX gene may be employed to produce sterile males which may be released as a means of genetic control. In the sterile insect technique, large numbers of insects are raised and sterilized before they are released. If sufficient numbers of insects are released, the females in the wild will mate with the released sterilized males and produce no viable offspring. This technique works best when only sterile males are released. A means to release only sterile males is to employ a gene that is lethal to females under certain conditions (i.e., a toxin gene), but not males. Expression of the lethal gene can be controlled by the female-specific enhancer from the *Drosophila* yp1 (yolk protein 1) gene, or the Yp3 fat body enhancer, for example. The use of a sex-specific promoter has been proposed for use in *Drosophila* (Heinrich et al., *Proc. Natl. Acad. Sci. U.S.A.* (2000) 97, 8229-8232; Thomas et al., *Science,* (2000) 287, 2474-2476). Suicide genes may also be introduced that can be activated by exposure to certain chemicals.

Also included herein are insecticidal polypeptides having the activity of a U-ACTX polypeptide. The activity of insect neurons is generated by precise regulation of the opening and closing of ion channels, including sodium channels, calcium channels, and calcium-activated potassium channels. The activity of U-ACTX polypeptide is demonstrated by rapid paralysis of insects, inhibition of insect voltage-gated calcium channels, or inhibition of high conductance calcium-activated potassium channels. Inhibition of calcium channels and calcium-activated potassium channels may be studied in isolated insect neurons, in recombinant cells expressing a channel, or a combination comprising one or more of the foregoing. In one embodiment, the calcium channels and/or the high conductance calcium-activated potassium channels are those naturally found in an insect neuronal system. In one embodiment, the U-ACTX polypeptide inhibits both a high conductance voltage-gated calcium channel and a calcium-activated potassium channel.

In one embodiment, the U-ACTX polypeptide blocks greater than or equal to about 50%, 60%, 70%, 75%, 80%, 85% or 95% of the calcium current in an insect voltage-gated calcium channel. In one embodiment, the insect voltage-gated calcium channel is one expressed in dorsal unpaired median (DUM) neurons of the American cockroach *Periplaneta americana.*

In another embodiment, the U-ACTX polypeptide blocks greater than or equal to about 50%, 60%, 70%, 75%, 80%, 85% or 95% of activity of an insect high conductance calcium-activated potassium channel. In one embodiment, the insect calcium-activated potassium channel comprises a *P. americana* high conductance calcium-activated potassium channel. In another embodiment, the channel is the $\alpha$ subunit of the *P. americana* pSlo channel as described previously (Derst et al. (2003) *Eur. J. Neurosci.* 17, 1197-1212)

In yet another embodiment, U-ACTX polypeptide blocks greater than or equal to about 50%, 60%, 70%, 75%, 80%, 85% or 95% of the calcium current in an insect voltage gated calcium channel and greater than or equal to about 70%, 75%, 80%, 85% or 95% of activity of an insect high conductance calcium-activated potassium channel.

The insecticidal polypeptides can be employed in a wide variety of methods as described in more detail below.

Libraries of mutated insecticidal polypeptides for the purposes of screening may be obtained by in vitro evolution of a gene for U-ACTX-Hv1a or a variant, as described previously for unrelated proteins. Libraries can be produced using error-prone PCR of the entire U-ACTX-Hv1a gene or variant gene or digestion of the U-ACTX-Hv1a gene or variant gene with an appropriate enzyme followed by error-prone PCR reconstruction of the entire gene sequence. These error-prone PCR procedures could also be applied to the complete prepro-polypeptide gene sequence for U-ACTX-Hv1a or a variant. The library of mutant U-ACTX-Hv1a or variant gene sequences could then be used to generate a series of U-ACTX-Hv1a variant antagonists. These antagonists may then be screened for their ability to inhibit the binding of U-ACTX-Hv1a, or a selected variant thereof, to its molecular target. Screening may be performed, for example, by phage display of a mutant gene library followed by selection of phage particles that bind tightly to the molecular target of U-ACTX, or phage particles that inhibit the binding of U-ACTX-Hv1a or the selected variant thereof, to the molecular target of U-ACTX. As would be understood by one of ordinary skill in the art, a mutant gene library could also be constructed by other standard molecular biological methods such as oligonucleotide cassette mutagenesis or construction of synthetic genes with certain nucleotide positions randomized.

U-ACTX, or its homologs, can be used to screen compound libraries for insecticidal molecules that bind to the same site on insect channels as U-ACTX. In one embodiment, screening is performed by selection of compounds that compete with the binding of U-ACTX to insect voltage-gated calcium channels or that cause the release of U-ACTX that is pre-bound to insect voltage-gated calcium channels. In another embodiment, screening is performed by selection of compounds that compete with the binding of U-ACTX to insect calcium-activated potassium channels or that cause the release of U-ACTX that is pre-bound to insect calcium-activated potassium channels. In yet another embodiment, screening may be performed, for example, by selection of compounds that prevent the binding of U-ACTX to insect calcium-activated potassium channels and also prevent the binding of U-ACTX to voltage-gated insect calcium channels, or by selection of compounds that cause the release of U-ACTX that is pre-bound to insect calcium-activated potassium channels and also cause the release of U-ACTX that is pre-bound to insect voltage-gated calcium channels.

A method of selecting a test compound that binds to an insect channel comprises providing the insect channel, wherein the insect channel is an insect voltage-gated calcium channel, an insect calcium-activated potassium channel, or a combination comprising one or more of the foregoing insect channels, and determining if the test compound competes with the binding of a U-ACTX peptide to the insect channel, wherein the U-ACTX peptide is greater than or equal to about 70% identical to SEQ ID NO:2 and has insecticidal activity. The method may further comprise testing the ability of the test compound to act as a blocker of insect calcium channels or a blocker of insect calcium-activated potassium channels or a blocker of both these types of channels.

A method of selecting a test compound that binds to an insect channel comprises providing the insect channel, wherein the insect channel is an insect voltage-gated calcium channel, an insect calcium-activated potassium channel, or a combination comprising one or more of the foregoing insect channels, and determining if the test compound releases at least a portion of a U-ACTX peptide pre-bound to the insect channel, wherein the U-ACTX peptide is greater than or equal to about 70% identical to SEQ ID NO:2 and has insecticidal activity. The method may further comprise testing the ability of the test compound to act as an blocker of insect calcium channels or a blocker of insect calcium-activated potassium channels or a blocker of both these types of channels.

Competition with a U-ACTX peptide or release of a pre-bound U-ACTX peptide can be determined by using a labeled U-ACTX peptide. For example, the fluorescent signal obtained from a fluorescently labeled U-ACTX will change depending upon the bound versus unbound state of the labeled peptide. Alternatively, release of a radiolabeled U-ACTX bound to a calcium channel upon binding of a test compound can be measured as the release of radiolabeled U-ACTX from the channel into, for example, the surrounding buffer solution.

A method of controlling an insect comprises contacting the insect or an insect larva with an insecticidally effective amount of a U-ACTX polypeptide. The U-ACTX polypeptide may be in the form of a purified polypeptide, a polynucleotide encoding the U-ACTX polypeptide optionally in an expression vector, an insect virus expressing the U-ACTX polypeptide, a cell such as a plant cell or a bacterial cell expressing the U-ACTX polypeptide, or a transgenic plant expressing the U-ACTX polypeptide. The U-ACTX polypeptide can also be fused to, or delivered in conjunction with, an agent that enhances the activity of the U-ACTX polypeptide when ingested by insects, such as snowdrop lectin. Contacting includes, for example, injection of the U-ACTX polypeptide, external contact, or ingestion of the U-ACTX polypeptide or polynucleotide or virus expressing the U-ACTX polypeptide.

A method of treating a plant comprises contacting the plant with an insecticidally effective amount of a U-ACTX polypeptide. The U-ACTX polypeptide may be in the form of a purified polypeptide, a polynucleotide encoding the U-ACTX polypeptide optionally in an expression vector, a virus expressing the U-ACTX polypeptide, or a cell such as a plant cell or a bacterial cell expressing the U-ACTX polypeptide.

In one embodiment, there is provided an insecticidal composition comprising a purified U-ACTX polypeptide and an agriculturally acceptable carrier, diluent and/or excipient. In another embodiment, an insecticidal composition comprises a virus expressing a U-ACTX polypeptide. Insect viruses can be replicated and expressed inside a host insect once the virus infects the host insect. Infecting an insect with an insect virus can be achieved via conventional methods, including ingestion, inhalation, direct contact of the insect or insect larvae with the insect virus, and the like.

The insecticidal composition may be in the form of flowable solution or suspension such as an aqueous solution or suspension. Such aqueous solutions or suspensions may be provided as a concentrated stock solution which is diluted prior to application, or alternatively, as a diluted solution ready-to-apply. In another embodiment, an insecticide composition comprises a water dispersible granule. In yet another embodiment, an insecticide composition comprises a wettable powder, dust, pellet, or colloidal concentrate. Such dry forms of the insecticidal compositions may be formulated to dissolve immediately upon wetting, or alternatively, dissolve in a controlled-release, sustained-release, or other time-dependent manner.

When the U-ACTX polypeptides can be expressed by an insect virus, the virus expressing the U-ACTX polypeptide can be applied to the crop to be protected. The virus may be engineered to express a U-ACTX polypeptide, either alone or in combination with one or several other U-ACTX polypeptides, or in combination with other insecticides such as other insecticidal polypeptide toxins that may result in enhanced or synergistic insecticidal activity. Suitable viruses include, but are not limited to, baculoviruses.

When the insecticidal compositions comprise intact cells (e.g., bacterial cells) expressing a U-ACTX polypeptide, such cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like), and combinations comprising one or more of the foregoing materials. The formulations may include spreader-sticker adjuvants, stabilizing agents, other pesticidal additives, surfactants, and combinations comprising one or more of the foregoing additives. Liquid formulations may be aqueous-based or non-aqueous and employed as foams, suspensions, emulsifiable concentrates, and the like. The ingredients may include rheological agents, surfactants, emulsifiers, dispersants, polymers, liposomes, and combinations comprising one or more of the foregoing ingredients.

Alternatively, the U-ACTX polypeptides may be expressed in vitro and isolated for subsequent field application. Such polypeptides may be in the form of crude cell lysates, suspensions, colloids, etc., or may be purified, refined, buffered, and/or further processed, before formulating in an active insecticidal formulation.

Regardless of the method of application, the amount of the active component(s) is applied at an insecticidally-effective amount, which will vary depending on such factors as, for example, the specific insects to be controlled, the specific plant or crop to be treated, the environmental conditions, and the method, rate, and quantity of application of the insecticidally-active composition.

Insecticidal compositions comprising the U-ACTX polypeptides, polynucleotides, cells, vectors, etc., can be formulated with an agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination another other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions may be applied to the environment of the target insect, for example onto the foliage of the plant or crop to be protected, by conventional methods, preferably by spraying. The strength and duration of insecticidal application may be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal compositions may be employed singly or in combination with other compounds, including and not limited to other pesticides. They may be used in conjunction with other treatments such as surfactants, detergents, polymers or time-release formulations. The insecticidal compositions may comprise an insect attractant. The insecticidal compositions may be formulated for either systemic or topical use. Such agents may also be applied to insects directly.

The concentration of the insecticidal composition that is used for environmental, systemic, or foliar application may vary depending upon the nature of the particular formulation, means of application, environmental conditions, and degree of biocidal activity.

Alternatively, a crop may be engineered to express U-ACTX, either alone, or in combination with other insecticidal polypeptide toxins that may result in enhanced or synergistic insecticidal activity. Crops for which this approach would be useful include, but are not limited to, cotton, tomato, sweet corn, lucerne, soybean; sorghum, field pea, linseed, safflower, rapeseed, sunflower, and field lupins.

Arthopods of suitable agricultural, household and/or medical/veterinary importance for treatment with the insecticidal polypeptides include, for example, members of the classes and orders: Coleoptera such as the American bean weevil *Acanthoscelides obtectus*, the leaf beetle *Agelastica alni*, click beetles (*Agriotes lineatus, Agriotes obscurus, Agriotes bicolor*), the grain beetle *Ahasverus advena*, the summer schafer *Amphimallon solstitialis*, the furniture beetle *Anobium punctatum, Anthonomus* spp. (weevils), the Pygmy mangold beetle *Atomaria linearis*, carpet beetles (*Anthrenus* spp., *Attagenus* spp.), the cowpea weevil *Callosobruchus maculatus*, the fried fruit beetle *Carpophilus hemipterus*, the cabbage seedpod weevil *Ceutorhynchus assimilis*, the rape winter stem weevil *Ceutorhynchus picitarsis*, the wireworms *Conoderus vespertinus* and *Conoderus falli*, the banana weevil *Cosmopolites sordidus*, the New Zealand grass grub *Costelytra zealandica*, the June beetle *Cotinis nitida*, the sunflower stem weevil *Cylindrocopturus adspersus*, the larder beetle *Dermestes lardarius*, the corn rootworms *Diabrotica virgifera, Diabrotica virgifera virgifera*, and *Diabrotica barberi*, the Mexican bean beetle *Epilachna varivestis*, the old house borer *Hylotropes bajulus*, the lucerne weevil *Hypera postica*, the shiny spider beetle *Gibbium psylloides*, the cigarette beetle *Lasioderma serricorne*, the Colorado potato beetle *Leptinotarsa decemlineata*, Lyctus beetles (*Lyctus* spp.), the pollen beetle *Meligethes aeneus*, the common cockshafer *Melolontha melolontha*, the American spider beetle *Mezium americanum*, the golden spider beetle *Niptus hololeucus*, the grain beetles *Oryzaephilus surinamensis* and *Oryzaephilus mercator*, the black vine weevil *Otiorhynchus sulcatus*, the mustard beetle *Phaedon cochleariae*, the crucifer flea beetle *Phyllotreta cruciferae*, the striped flea beetle *Phyllotreta striolata*, the cabbage steam flea beetle *Psylliodes chrysocephala, Ptinus* spp. (spider beetles), the lesser grain borer *Rhizopertha dominica*, the pea and been weevil *Sitona lineatus*, the rice and granary beetles *Sitophilus oryzae* and *Sitophilus granarius*, the red sunflower seed weevil *Smicronyx fulvus*, the drugstore beetle *Stegobium paniceum*, the yellow mealworm beetle *Tenebrio molitor*, the flour beetles

*Tribolium castaneum* and *Tribolium confusum*, warehouse and cabinet beetles (*Trogoderma* spp.), and the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*, the German cockroach *Blatella germanica*, the Madeira cockroach *Leucophaea maderae*, the American cockroach *Periplaneta americana*, and the smokybrown cockroach *Periplaneta fuliginosa*; Diplopoda such as the spotted snake millipede *Blaniulus guttulatus*, the flat-back millipede *Brachydesmus superus*, and the greenhouse millipede *Oxidus gracilis*; Diptera such as the African tumbu fly (*Cordylobia anthropophaga*), biting midges (*Culicoides* spp.), bee louse (*Braula* spp.), the beet fly *Pegomyia betae*, black flies (*Cnephia* spp., *Eusimulium* spp., *Simulium* spp.), bot flies (*Cuterebra* spp., *Gastrophilus* spp., *Oestrus* spp.), craneflies (*Tipula* spp.), eye gnats (*Hippelates* spp.), filth-breeding flies (*Calliphora* spp., *Fannia* spp., *Hermetia* spp., *Lucilia* spp., *Musca* spp., *Muscina* spp., *Phaenicia* spp., *Phormia* spp.), flesh flies (*Sarcophaga* spp., *Wohlfahrtia* spp.); the frit fly *Oscinella frit*, fruitflies (*Dacus* spp., *Drosophila* spp.), head and canon flies (*Hydrotea* spp.), the hessian fly *Mayetiola destructor*, horn and buffalo flies (*Haematobia* spp.), horse and deer flies (*Chrysops* spp., *Haematopota* spp., *Tabanus* spp.), louse flies (*Lipoptena* spp., *Lynchia* spp., and *Pseudolynchia* spp.), medflies (*Ceratitus* spp.), mosquitoes (*Aedes* spp., *Anopheles* spp., *Culex* spp., *Psorophora* spp.), sandflies (*Phlebotomus* spp., *Lutzomyia* spp.), screw-worm flies (*Chrysomya bezziana* and *Cochliomyia hominivorax*), sheep keds (*Melophagus* spp.); stable flies (*Stomoxys* spp.), tsetse flies (*Glossina* spp.), and warble flies (*Hypoderma* spp.); Isoptera (termites) including species from the families Hodotermitidae, Kalotermitidae, Mastotermitidae, Rhinotennitidae, Serritermitidae, Termitidae, Termopsidae; Heteroptera such as the bed bug *Cimex lectularius*, the cotton stainer *Dysdercus intermedius*, the Sunn pest *Eurygaster integriceps*, the tarnished plant bug *Lygus lineolaris*, the green stink bug *Nezara antennata*, the southern green stink bug *Nezara viridula*, and the triatomid bugs *Panstrogylus megistus, Rhodnius ecuadoriensis, Rhodnius pallescans, Rhodnius prolixus, Rhodnius robustus, Triatoma dimidiata, Triatoma infestans*, and *Triatoma sordida*; Homoptera such as the California red scale *Aonidiella aurantii*, the black bean aphid *Aphis fabae*, the cotton or melon aphid *Aphis gossypii*, the green apple aphid *Aphis pomi*, the citrus spiny whitefly *Aleurocanthus spiniferus*, the oleander scale *Aspidiotus hederae*, the sweet potato whitefly *Bemesia tabaci*, the cabbage aphid *Brevicoryne brassicae*, the pear psylla *Cacopsylla pyricola*, the currant aphid *Cryptomyzus ribis*, the grape phylloxera *Daktulosphaira vitifoliae*, the citrus psylla *Diaphorina citri*, the potato leafhopper *Empoasca fabae*, the bean leafhopper *Empoasca solana*, the vine leafhopper *Empoasca vitis*, the woolly aphid *Eriosoma lanigerum*, the European fruit scale *Eulecanium corni*, the mealy plum aphid *Hyalopterus arundinis*, the small brown planthopper *Laodelphax striatellus*, the potato aphid *Macrosiphum euphorbiae*, the green peach aphid *Myzus persicae*, the green rice leafhopper *Nephotettix cinticeps*, the brown planthopper *Nilaparvata lugens*, gall-forming aphids (*Pemphigus* spp.), the hop aphid *Phorodon humuli*, the bird-cherry aphid *Rhopalosiphum padi*, the black scale *Saissetia oleae*, the greenbug *Schizaphis graminum*, the grain aphid *Sitobion avenae*, and the greenhouse whitefly *Trialeurodes vaporariorum*; Isopoda such as the common pillbug *Armadillidium vulgare* and the common woodlouse *Oniscus asellus*; Lepidoptera such as *Adoxophyes orana* (summer fruit tortrix moth), *Agrotis ipsolon* (black cutworm), *Archips podana* (fruit tree tortrix moth), *Bucculatrix pyrivorella* (pear leafminer), *Bucculatrix thurberiella* (cotton leaf perforator), *Bupalus piniarius* (pine looper), *Carpocapsa pomonella* (codling moth), *Chilo suppressalis* (striped rice borer), *Choristoneura fumiferana* (eastern spruce budworm), *Cochylis hospes* (banded sunflower moth), *Diatraea grandiosella* (southwestern corn borer), *Earis insulana* (Egyptian bollworm), *Euphestia kuehniella* (Mediterranean flour moth), *Eupoecilia ambiguella* (European grape berry moth), *Euproctis chrysorrhoea* (brown-tail moth), *Euproctis subflava* (oriental tussock moth), *Galleria mellonella* (greater wax moth), *Helicoverpa armigera* (cotton bollworm), *Helicoverpa zea* (cotton bollworm), *Heliothis virescens* (tobacco budworm), *Hofmannophila pseudopretella* (brown house moth), *Homeosoma electellum* (sunflower moth), *Homona magnanima* (oriental tea tree tortrix moth), *Lithocolletis blancardella* (spotted tentiform leafminer), *Lymantria dispar* (gypsy moth), *Malacosoma neustria* (tent caterpillar), *Mamestra brassicae* (cabbage armyworm), *Mamestra configurata* (Bertha armyworm), the hornworms *Manduca sexta* and *Manuduca quinquemaculata, Operophtera brumata* (winter moth), *Ostrinia nubilalis* (European corn borer), *Panolis flammea* (pine beauty moth), *Pectinophora gossypiella* (pink bollworm), *Phyllocnistis citrella* (citrus leafminer), *Pieris brassicae* (cabbage white butterfly), *Plutella xylostella* (diamondback moth), *Rachiplusia ni* (soybean looper), *Spilosoma virginica* (yellow bear moth), *Spodoptera exigua* (beet armyworm), *Spodoptera frugiperda* (fall armyworm), *Spodoptera littoralis* (cotton leafworm), *Spodoptera litura* (common cutworm), *Spodoptera praefica* (yellowstriped armyworm), *Sylepta derogata* (cotton leaf roller), *Tineola bisselliella* (webbing clothes moth), *Tineola pellionella* (case-making clothes moth), *Tortrix viridana* (European oak leafroller), *Trichoplusia ni* (cabbage looper), *Yponomeuta padella* (small ermine moth); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviates*, the southern mole cricket *Scapteriscus borellii*, the tawny mole cricket *Scapteriscus vicinus*, and the desert locust *Schistocerca gregaria*; Phthiraptera such as the cattle biting louse *Bovicola bovis*, biting lice (*Damalinia* spp.), the cat louse *Felicola subrostrata*, the shortnosed cattle louse *Haematopinus eurysternus*, the tail-switch louse *Haematopinus quadripertussus*, the hog louse *Haematopinus suis*, the face louse *Linognathus ovillus*, the foot louse *Linognathus pedalis*, the dog sucking louse *Linognathus setosus*, the long-nosed cattle louse *Linognathus vituli*, the chicken body louse *Menacanthus stramineus*, the poultry shaft louse *Menopon gallinae*, the human body louse *Pediculus humanus*, the pubic louse *Phthirus pubis*, the little blue cattle louse *Solenopotes capillatus*, and the dog biting louse *Trichodectes canis*; Psocoptera such as the booklice *Liposcelis bostrychophila, Liposcelis decolor, Liposcelis entomophila*, and *Trogium pulsatorium*; Siphonaptera such as the bird flea *Ceratophyllus gallinae*, the dog flea *Ctenocephalides canis*, the cat flea *Ctenocephalides felis*, the human flea *Pulex irritans*, and the oriental rat flea *Xenopsylla cheopis*; Symphyla such as the garden symphylan *Scutigerella immaculata*; Thysanura such as the gray silverfish *Ctenolepisma longicaudata*, the four-lined silverfish *Ctenolepisma quadriseriata*, the common silverfish *Lepisma saccharina*, and the firebrat *Thermobia domestica*; Thysanoptera such as the tobacco thrips *Franklin-*

*iella fusca*, the flower thrips *Frankliniella intonsa*, the western flower thrips *Frankliniella occidentalis*, the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing insects.

In one embodiment, the insecticidal compositions comprising the U-ACTX polypeptides, polynucleotides, cells, vectors, etc., can be employed to treat ectoparasites. Ectoparasites include, for example, fleas, ticks, mange, mites, mosquitoes, nuisance and biting flies, lice, and combinations comprising one or more of the foregoing ectoparasites. The term fleas includes the usual or accidental species of parasitic flea of the order Siphonaptera, and in particular the species *Ctenocephalides*, in particular *C. felis* and *C. canis*, rat fleas (*Xenopsylla cheopis*) and human fleas (*Pulex irritans*). Ectoparasites on farm animals (e.g., cattle), companion animals (e.g., cats and dogs), and human may be treated. In the case of farm and domestic animals, treatment may include impregnation in a collar or topical application to a localized region followed by diffusion through the animal's dermis. In the case of a human, treatment may include a composition suitable for the treatment of lice in humans. Such a composition may be suitable for application to a human scalp such as a shampoo or a conditioner.

The invention is further illustrated by the following non-limiting examples.

EXAMPLES

Example 1

Identification of U-ACTX-Hv1a and homologs

A female *Hadronyche versuta* spider was obtained from the Blue Mountains region of New South Wales, Australia. Male and female *Atrax robustus* spiders were collected from the Sydney metropolitan area of New South Wales, Australia. The specimens were housed in airtight collection jars until extraction of venom glands. The funnel web spiders were cooled to −20° C. for 40 to 60 minutes. Venom glands were independently dissected from each specimen. Each pair of venom glands was independently placed in extraction buffer (Amersham Pharmacia Biotech).

Immediately following venom gland isolation, poly A+ mRNA was prepared using a QuickPrep Micro mRNA Purification Kit (Amersham Pharmacia Biotech). The purified mRNA samples were washed with 80% ethanol and dried with a Speedvac. 10 microliters (μl) of RNAse-free distilled water was used to rehydrate the mRNA samples. The purified mRNA samples were stored at −20° C.

Thereafter, cDNA libraries were constructed using a Marathon cDNA Amplification Kit (CLONTECH). Briefly, polyA+ RNA is was isolated from which ds cDNA was formed. The cDNA was ligated to adaptor DNAs to form a library of adaptor cDNA molecules. From the adapted mRNA template, single-stranded cDNA were constructed using Superscript III reverse transcriptase (Life Technologies, Inc) and Echoclonanch-2 primer, a poly (dT) anchor primer ($GGGCAGGT_{17}$). Second strand synthesis was carried out according to the kit specifications. cDNA products were purified using Concert Rapid PCR Purification kit, a high yield purification cartridge (GIBCO). The double stranded cDNA was eluted with 50 μl of Tris-EDTA buffer (10 mM) Tris-Cl, 1 mM EDTA, pH 8.0).

The Marathon cDNA Amplification adaptor (CLONTECH) was then ligated to the double stranded cDNA. The ligation reaction was allowed to proceed at 16° C. overnight. After overnight ligation, the sample was precipitated using 10 μl of a 1 to 20 dilution of glycogen, 10 μl of 3 M sodium acetate pH 5.2, and 100 μl of 100% cold ethanol. Subsequently, the sample was washed with 80% ethanol and dried for 10 minutes prior to resuspension in 200 μl of Tris-EDTA buffer.

Leader sequence information was obtained using 5' RACE (Rapid Amplification of cDNA Ends; see Frohman et al. (1988) *Proc. Natl. Acad. Sci. U.S.A.* 85, 8993-9002). Redundant polymerase chain reaction (PCR) primers were designed for this technique. The redundant primers were used in conjunction with a 5' universal adaptor primer (EchoAP1) in order to obtain unknown leader sequence information. Primers for 3' RACE were designed from the cDNA leader sequence obtained from 5' RACE. 3' RACE primers were used in combination with a universal adaptor oligo d(T) primer (CLONTECH) to generate gene products that have a signal sequence homologous with that of U-ACTX-Hv1a. All primers not included in kits were constructed by PROLIGO Ltd. The 5' RACE primers were:

```
SEQ ID NO: 29:
CACCCCTAATACGACTCACTATAGG

SEQ ID NO: 30:
(A/G)TTNCC(A/G)TT(T/C)TC(A/G)TT(T/C)TC(T/C)TC(A/G)
AA
```

The 3' RACE primers were:

```
SEQ ID NO: 31:    TGCTGCAATATGAATACCGC

SEQ ID NO: 32:    GGGCAGGTTTTTTTTTTTTTTTTT
```

PCR reactions were conducted using 5 μl double stranded cDNA, 27 μl Milli Q water, 25 mM $MgCl_2$, 10×PCR buffer, 50×dNTPs, and 5 μl AMPLI$_{GOLD}$TAQ Enzyme (Perkin Elmer, AmpliTaq Gold with GeneAmp Kit). PCR reactions were run on a thermal cycler using following the protocol (Table 1):

TABLE 1

Thermal cycling protocol for PCR reactions

| Cycle Temperature | Time | Number of Cycles |
|---|---|---|
| 95° C. | 5 minutes | 1 |
| 95° C. | 30 seconds | 35 |
| 55° C. | 60 seconds | 35 |
| 72° C. | 90 seconds | 35 |
| 72° C. | 10 minutes | 1 |
| 30° C. | 1 minutes | 1 |

Amplified cDNA products were electrophoresed on a 1.5% agarose gel and stained with ethidium bromide for size verification.

Verified PCR products were extracted from the agarose gel using a GIBCO gel purification kit and precipitated using Pellet Paint Co-Precipitant kit (Novagen). Once precipitated, cDNA ends were phosphorylated with kinase in preparation for cloning. Samples were ligated into the pSMART vector and transformed into *E. cloni* cells (Lucigen) using the Lucigen CloneSmart Blunt Cloning kit. Successfully transformed clones were cultured for one hour in Terrific Broth with 50 μg/mL ampicillin, and then plated to allow for overnight growth.

The samples were tested for the correct insert size by PCR and gel electrophoresis. Samples containing the correct insert size were submitted for DNA sequencing. Complete cDNA sequences encoding the prepropolypeptide form of U-ACTX-Hv1a (SEQ ID No:1) and eight homologs thereof (SEQ ID NO:5, 8, 11, 14, 17, 20, 23, and 26) were obtaining from sequencing numerous clones.

The prepropolypeptides sequences are summarized in FIG. 1. The signal peptide cleavage site in these prepropolypepides was predicted using version 3.0 of the SignalP program (Dryløv et al., Improved prediction of signal peptides: SignalP 3.0, *Journal of Molecular Biology* (2004) 340, 783-795. The mature polypeptide is predicted to result from cleavage of the propolypeptide following the dibasic Arg-Arg sequence at positions 36-37, as for the known propolypeptide cleavage site in the ω-ACTX-1 polypeptides produced by the same spiders. These two endoproteolytic cleavage sites are indicated by arrows in FIG. 1.

Example 2

Preparation of a Recombinant Form of U-ACTX-Hv1a

A synthetic gene encoding residues 3 to 39 of the predicted mature polypeptide region of U-ACTX-Hv1a was designed by annealing, extension, and amplification of overlapping oligonucleotides (see FIG. 2). In the first step, four oligonucleotides encoding residues 3 to 39 of U-ACTX-Hv1a were annealed and extended with Pfu polymerase. Codon usage in the four oligonucleotides was optimized for optimal expression in *Escherichia coli*. The four oligonucleotides are designated:

```
FW178-1 (SEQ ID NO: 33):
TGCGTTCCGGTTGACCAGCCGTGCTCCCTGAACACCCAGCCG,

FW178-2 (SEQ 1D-NO: 34):
CGTTACGCTCCTGGGTGCAGGTAGCGTCGTCGCAGCACGGCTGGGTGTTC
AGGGAGC

FW178-3 (SEQ ID NO: 35):
CGCTACCTGCACCCAGGAGCGTAACGAAAACGGTCACACCGTTTACTACT
GCCG,
and

FW178-R (SEQ D NO: 36):
GAATTCTCAAGCACGGCAGTAGTAAACGG
```

The four oligonucleotides were added at a final concentration of 2 μM in 50 μl of reaction buffer. The reaction also contained 400 μM dNTP mix (Invitrogen). The annealing reaction proceeded at 60° C. for 15 minutes. The temperature was then raised to 72° C., and the mixture was further incubated for 30 minutes following the addition of 2.5 units of Pfu polymerase (Stratagene).

In the second step, 20 μl of the reaction mixture was used as a template for a standard PCR amplification of the entire coding sequence with primers FW178-F (SEQ ID NO: 37: cgggatccTGCGTTCCGGTTGACCAGCCG) and FW178-R (SEQ ID NO: 34) (see FIG. 2). These primers contain a 5' BamHI and 3' EcoRI site, respectively, for cloning purposes. The amplified PCR product was digested with BamHI and EcoRI and subcloned into BamHI/EcoRI digested PGEX-2T vector using standard methods. The resulting plasmid (pBLS1) encodes residues 3 to 39 of the mature polypeptide sequence of U-ACTX-Hv1a as an in-frame fusion to the C-terminus of *Schistosoma japonicum* glutathione S-transferase (GST). A thrombin cleavage site located between the GST and U-ACTX-Hv1a coding regions enables the polypeptide to be liberated from the fusion protein by thrombin cleavage. The liberated polypeptide contains the dipeptide sequence Gly-Ser (a vestige of the thrombin cleavage site) appended at the N-terminus of residues 3 to 39 of U-ACTX-Hv1a; we refer to this 39-residue polypeptide as rU-ACTX-Hv1a.

*Escherichia coli* BL21 cells were transformed with pBLS1 for overproduction of the GST:rU-ACTX-Hv1a fusion protein. The cells were grown in LB medium at 37° C. to an $OD_{600}$ of 0.6 to 0.8 before induction of the fusion protein with 300 μM isopropyl-β-D-thiogalactopyranoside (IPTG). The cells were harvested by centrifugation at an $OD_{600}$ of 1.9-2.2 and then lysed by sonication. The recombinant fusion polypeptide was purified from the soluble cell fraction using affinity chromatography on GSH-Sepharose (Amersham Biosciences) and then cleaved on the column by the addition of bovine thrombin (Sigma) for about 24 hours. The unbound U-ACTX polypeptide was eluted from the column with Tris-buffered saline (150 mM NaCl, 50 mM Tris, pH 8.0) and immediately purified using reverse phase high-performance liquid chromatography (rpHPLC). Recombinant U-ACTX polypeptide and contaminants were eluted from a Vydac $C_{18}$ analytical rpHPLC column (4.6×250 mm, 5 μm pore size) at a flow rate of 1 ml/min using a linear gradient of 10-32% acetonitrile over 20 minutes. A single major peak corresponding to rU-ACTX-Hv1a eluted at a retention time of approximately 9 minutes. Electrospray mass spectral analysis of the rpHPLC-purified U-ACTX polypeptide returned a molecular mass of 4273 Da, which is identical to the predicted molecular mass of fully oxidized rU-ACTX-Hv1a in which the six cysteines form three disulfide bonds.

Example 3

Recombinant U-ACTX-Hv1a is Lethal to Insects

The insecticidal activity of rU-ACTX-Hv1a was determined quantitatively by direct injection of polypeptides dissolved in insect saline into *Musca domestica* (house flies). Flies of undetermined sex (body weight 10 to 25 mg) were injected with 1 to 2 μl of polypeptide at concentrations ranging from 10 to $10^5$ pmol/g. Control flies were injected with 2 μl of insect saline. Ten flies were injected at each concentration of polypeptide. An Arnold microapplicator (Burkard Scientific Supply, Rickmansworth, England) equipped with a 29-gauge needle was used to administer dorsal thoracic injections. Specimens were temporarily immobilized at 4° C. for the injections and then immediately returned to room temperature (24° C.).

FIG. 3 shows the dose-response curve for rU-ACTX-Hv1a obtained using this method. Each point represents the average of three independent measurements performed on different days. The $LD_{50}$ value (i.e., the dose of rU-ACTX-Hv1a that kills 50% of flies at 24 hours post-injection) was calculated by fitting the following equation to the log dose-response curve:

$$y=(a-b)/[1+(x/LD_{50})^n]$$

where y is the percentage deaths in the sample population at 24 hours post-injection, x is the toxin dose in pmol $g^{-1}$, n is a variable slope factor, a is the maximum response and b is the minimum response. The calculated $LD_{50}$ value of 100±4 pmol/g makes rU-ACTX-Hv1a one of the most potent insecticidal peptide toxins discovered to date.

Example 4

Determination of the Molecular Targets of rU-ACTX-Hv1a—Experiments with DUM Neurons from the American cockroach *Periplaneta americana*

Protocols

DUM neurons from *P. americana* contain calcium channels from which $Ca_v$ channel currents ($I_{Ca}$) can be recorded using whole-cell patch-clamp recording techniques. DUM neuron cell bodies were isolated from the midline of the terminal abdominal ganglion (TAG) of the nerve cord of *P. Americana*. Cockroaches were anaesthetized by cooling at −20° C. for approximately 5 minutes. They were then pinned dorsal side up on a dissection dish, and the dorsal cuticle, gut contents, and longitudinal muscles were removed. The ganglionic nerve cord was identified, and the TAG was carefully removed and placed in normal insect saline (NIS) containing 200 mM NaCl, 3.1 mM KCl, 5 mM $CaCl_2$, 4 mM $MgCl_2$, 10 mM N-[2-hydroxyethyl]piperazine-N'-2-ethanesulfonic acid] (HEPES), 50 mM sucrose, with 5% volume/volume bovine calf serum and 50 IU $ml^{-1}$ penicillin and 50 μg $ml^{-1}$ streptomycin (Trace Biosciences, Noble Park, Australia) added, and the pH adjusted to 7.4 using NaOH.

The TAG was carefully dissected and placed in sterile $Ca^{2+}/Mg^{2+}$-free insect saline containing 200 mM NaCl, 3.1 mM KCl, 10 mM HEPES, 60 mM sucrose, 50 IU/mL penicillin, and 50 IU/ml streptomycin, with the pH adjusted to 7.4 using NaOH. The ganglia were then desheathed and incubated for 20 minutes in $Ca^{2+}/Mg^{2+}$-free insect saline containing 1.5 mg/ml collagenase. The ganglia were rinsed three times in normal insect saline. The resulting suspension was distributed into eight wells of a 24-well cluster plate. Each well contained a 12-mm diameter glass coverslip that had been previously coated with concanavalin A (2 mg/ml). Isolated cells were allowed to attach to coverslips overnight in an incubator (100% relative humidity, 37° C.).

Electrophysiological experiments employed the patch-clamp recording technique in whole-cell configuration to measure voltage-gated sodium, potassium, and calcium currents from cockroach DUM neurons. Coverslips with isolated cells were transferred to a 1-ml glass-bottom perfusion chamber mounted on the stage of a phase-contrast microscope. Whole-cell recordings of sodium, potassium, and calcium currents were made using an Axopatch 200A-integrating amplifier (Axon Instruments, Foster City, Calif.). Borosilicate glass-capillary tubing (Harvard Apparatus Ltd, Kent, UK) was used to pull single-use recording micropipettes.

The contents of the external and internal solutions were varied according to the type of recording procedure undertaken and also the particular ionic current being studied. The contents of all internal and external solutions used in voltage-clamp electrophysiological studies are detailed in Tables 2 to 4. In all experiments the holding potential was −80 mV. Electrode tip resistances were always in the range 0.8-4.0 MΩ. The osmolarity of both external and internal solutions was adjusted to 310 mosmol/liter with sucrose to reduce osmotic stress. The liquid junction potential between internal and external solutions was determined using the program JPCalc (Barry (1994) *J. Neurosci. Method.* 51, 107-116), and all data were compensated for this value.

TABLE 2

Composition of external and internal solutions used for electrophysiological recordings of potassium currents from cockroach DUM neurons

| Voltage-clamp | Solution No. | Constituents |
|---|---|---|
| Physiological external solution | 1 | 100 mM NaCl, 3.1 mM KCl, 5 mM $CaCl_2$, 4 mM $MgCl_2$, 10 mM HEPES[1], 10 mM glucose, 150 nM tetrodotoxin |
| $I_{K(total)}$ solution | 2 | Same as Solution No. 1 except 30 mM KCl externally |
| $I_{K(DR)}$ solution | 3 | Same as Solution No. 1 plus 30 nM charybdotoxin, 1 mM $Cd^{2+}$, and 5 mM 4-aminopyridine |
| $I_{K(A)}$ solution | 4 | Same as Solution No. 1 plus 30 nM charybdotoxin, 1 mM $Cd^{2+}$, and 5 mM TEA-Cl[2] |
| $I_{K(Ca)}$ solution | 5 | Same as Solution No. 1 but 75 mM KCl internally and externally 10 mM KCl and 5 mM 4-aminopyridine |
| Complete block of $I_K$ | 6 | Same as Solution No. 1 plus 30 nM charybdotoxin, 1 mM $Cd^{2+}$, 5 mM 4-aminopyridine, and 50 mM TEA-Cl |
| Internal solution | 7 | 135 mM KCl, 25 mM KF, 9 mM NaCl, 3 mM Mg-ATP, 1 mM $MgCl_2$, 0.1 mM $CaCl_2$, 1 mM EGTA[3], and 10 mM HEPES |

[1]HEPES = N-(2-hydroxyethyl)piperazine-N'-[2-ethanesulfonic acid];
[2]TEA-Cl = tetraethylammonium chloride;
[3]EGTA = Ethyleneglycol-bis(β-aminoethyl)-N,N,N',N'-tetraacetic acid

TABLE 3

Composition of external and internal solutions used for electrophysiological recordings of sodium currents from cockroach DUM neurons

| Voltage-clamp | Solution No. | Constituents |
|---|---|---|
| $I_{Na}$ external solution | 1 | 130 mM NaCl, 5 mM $CsCl_2$, 1.8 mM $CaCl_2$, 20 mM TEA-Cl[1], 5 mM 4-aminopyridine, 10 mM HEPES[2], 0.01 mM verapamil, 0.1 mM $NiCl_2$, 1 mM $CdCl_2$ |
| $I_{Na}$ internal solution | 2 | 135 mM CsF, 1 mM $MgCl_2$, 20 mM NaCl, 10 mM HEPES, 5 mM EGTA[3] |

[1]TEA-Cl = tetraethylammonium chloride;
[2]HEPES = N-(2-hydroxyethyl)piperazine-N'-[2-ethanesulfonic acid];
[3]EGTA = Ethyleneglycol-bis(β-aminoethyl)-N,N,N',N'-tetraacetic acid

TABLE 4

Composition of external and internal solutions used for electrophysiological recordings of calcium currents from cockroach DUM neurons

| Voltage-clamp | Solution No. | Constituents |
|---|---|---|
| $I_{Ca}$ external solution | 1 | 5 mM $CaCl_2$, 20 mM TEA-Br[1], 10 mM HEPES[2], 160 mM sodium acetate, 150 nM tetrodotoxin |
| $I_{Ca}$ internal solution | 2 | 110 mM CsCl, 0.5 mM $CaCl_2$, 10 mM HEPES, 10 mM sodium acetate, 50 mM TEA-Br, 10 mM EGTA[3], 2 mM Na-ATP |

[1]TEA-Br = tetraethylammonium bromide;
[2]HEPES = N-(2-hydroxyethyl)piperazine-N'-[2-ethanesulfonic acid];
[3]EGTA = Ethyleneglycol-bis(β-aminoethyl)-N,N,N',N'-tetraacetic acid Large tear-shaped DUM neurons with diameters greater than 45 μm were selected for experiments. Inverted voltage-clamp command pulses were applied to the bath through an Ag/AgCl pellet/3 M KCl-agar bridge. After formation of a gigaohm seal, suction was applied to break through the membrane. Experiments did not commence for a period of 5 to 10 minutes to allow for complete block of unwanted currents. Individual experiments were rejected if there were large leak currents or currents showed signs of poor space clamping such as an abrupt activation of currents upon relatively small depolarizing pulses. All chemicals were analytical grade and were supplied by Sigma Chemicals with the exception of tetrodotoxin which was from Alomone Labs (Jerusalem, Israel). Data, when quantified, are expressed as mean±standard error.

Stimulation and recording were both controlled by an Axo-Data data acquisition system (Axon Instruments) running on an Apple Macintosh computer. Data was filtered at 5 kHz (low-pass Bessel filter) and digital sampling rates were between 15 and 25 kHz depending on the length of the voltage protocol. Leakage and capacitive currents were digitally subtracted with P-P/4 procedures. Data analysis was performed off-line following completion of the experiment. I/V data were fitted by nonlinear regression of the following equation onto the data:

$$I=g_{max}\{1-(1/(1+\exp[V-V_{1/2})/s]))\}(V-V_{rev})$$

where I is the amplitude of the peak current at a given potential, V; $g_{max}$ is the maximal conductance; $V_{1/2}$ is the voltage at half-maximal activation; s is the slope factor; and $V_{rev}$ is the reversal potential.

Results $Ca_v$ channel currents ($I_{Ca}$) were recorded from *P. americana* DUM neurons using whole-cell patch-clamp recording techniques. DUM neurons produce inward tetrodotoxin (TTX)-sensitive sodium channel current ($I_{Na}$) and numerous voltage-gated potassium channel currents ($I_K$) following depolarizing test pulses. These currents were blocked using a combination of TTX, tetraethylammonium (TEA), and Cs, thus leaving intact currents flowing through $Ca_v$ channels.

Once $Ca_v$ channel currents were isolated, various concentrations of rU-ACTX-Hv1a were applied to the DUM neurons. At a concentration of 1 μM, rU-ACTX-Hv1a blocked the majority of $Ca_v$ currents in DUM neurons. The dose-response curve (FIG. 4) indicates that rU-ACTX-Hv1a blocks $Ca_v$ currents in DUM neurons with an $IC_{50}$ of 409 nM. There were no significant depolarizing shifts in the voltage-dependence of channel activation, as evidenced by the current-voltage ($I_{Ca}$/V) plots, indicating that rU-ACTX-Hv1a is a pore blocker as opposed to a gating modifier.

In contrast with the effects on calcium currents, rU-ACTX-Hv1a was found to have no effect on sodium currents in DUM neurons at concentrations up to 1 μM.

Example 5

Determination of the Molecular Targets of rU-ACTX-Hv1a—Experiments with Heterologously Expressed Cockroach pSlo Channels Protocols Human embryonic kidney (HEK293) cells (American Type Culture Collection, Bethesda, Md., USA) were maintained in Dulbecco's Modified Eagle's Medium (DMEM/High Modified, JRH Biosciences, Lenexa Kans., USA) supplemented with 10% bovine calf serum. Expression of pSlo channels (*P. americana* high conductance calcium-activated potassium channel channels) was performed by transfection of the HEK293 cells with a construct containing the pSlo coding region cloned into the expression vector pcDNA3.1, which also carries the G418 resistance gene (Invitrogen BV, San Diego, Calif., USA). HEK293 monolayers in 35 $mm^2$ dishes were transfected using 9 μl Lipofectamine Reagent (Gibco, BRL) and 5 μg DNA. Stably transfected cells were then selected with 1000 μg $ml^{-1}$ G418 (Gibco, Grand Island, N.Y., USA). These cells were maintained in the normal growth media described above and cultured on sterile glass coverslips to be used for the patch clamp experiments described below.

Whole-cell pSlo channel currents were measured at room temperature using borosilicate pipettes (Harvard Apparatus Ltd, Kent, UK) with resistances of 2-4 MΩ. Current measurements were made using an Axopatch 200A-integrating amplifier (Axon Instruments, Foster City, Calif., USA). In all experiments the holding potential was −90 mV. To record pSlo whole-cell currents, pipettes were filled with a solution containing 4 mM NaCl, 140 mM KCl, 2 mM ATP-$Mg_2$, 0.6 mM $CaCl_2$, and 10 mM N-(2-hydroxyethyl)piperazine-N'-[2-ethanesulfonic acid] (HEPES), with the pH adjusted to 7.25 with 2 M KOH. The external solution contained 135 mM NaCl, 5 mM KCl, 1 mM $MgCl_2$, 1 mM $CaCl_2$, 0.33 mM $NaH_2PO_4$, 10 mM glucose, and 10 mM HEPES, with the pH adjusted to 7.4 with 2 M NaOH. The osmolarity was approximately 290 mosmol/L. After breaking through the membrane, experiments did not commence for a period of 10-15 min to allow formation of >2 MΩ seals.

Results

The effect of rU-ACTX-Hv1a on $I_{K(Ca)}$ in HEK293 cells expressing the α-subunit of the *P. americana* high conductance calcium-activated potassium channel (pSlo) was tested. Addition of 1 μM rU-ACTX-Hv1a to pSlo channel-expressing HEK293 cells caused about a 77% block of $I_{K(Ca)}$. This is similar to the about 80% block previously reported for addition of 1 μM charybdotoxin to HEK293 cells expressing pSlo channels (Derst et al. (2003) *European Journal of Neuroscience* 17, 1197-1212). The dose-response curve (FIG. 5) indicates that rU-ACTX-Hv1a blocks pSlo currents with an $IC_{50}$ of 579 nM. Thus, it appears that rU-ACTX-Hv1a targets both insect $Ca_v$ and $K_{Ca}$ channels. rU-ACTX-Hv1a appears to act as a pore blocker, rather than a gating modifier, since there were no significant depolarizing shifts in the voltage dependence of channel activation.

Without being held to theory, it is believed that the marked potency of rU-ACTX-Hv1a results from a synergistic effect on insect $Ca_v$ and $K_{Ca}$ channels. These channels have long been known to be physiologically coupled and recent evidence suggests that they are in fact physically associated in the membrane. In addition to directly blocking the pore of insect $K_{Ca}$ channels, rU-ACTX-Hv1a may indirectly decrease currents through these channels by blocking the inward flow of calcium through $Ca_v$ channels, thus decreasing the local pool of intracellular calcium available to activate the $K_{Ca}$ channel. Thus, the action of rU-ACTX-Hv1a on $Ca_v$ channels potentiates its block of insect $K_{Ca}$ channels.

Novel polypeptides having insecticidal activity have been described. The polypeptides may be in prepropolypeptide, propolypeptide, or mature polypeptide form. The polypeptides, polynucleotides encoding the polypeptides optionally in an expression vector, an insect virus, viral vectors encoding the polypeptides, and cells expressing the polypeptides may be employed as insecticides. Advantages of the disclosed polypeptides over conventional insecticides include potency of the insecticides combined with differential toxicity between insects and vertebrates.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. All ranges disclosed herein are inclusive and combinable.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

We claim:

1. A purified polypeptide comprising an amino acid sequence having greater than or equal to about 90% identity to SEQ ID NO: 2, a molecular mass of approximately 4,300 Daltons, wherein said polypeptide has insecticidal activity.

2. The purified polypeptide of claim 1 wherein said sequence is selected from the group consisting of SEQ IDNOs: 3, 9, 12, 15, 18, 21, 24 and 27.

3. The purified polypeptide of claim 2, further comprising a propeptide sequence, a signal peptide sequence, or a combination thereof.

4. An insecticidal composition comprising an insecticidally effective amount of the purified polypeptide of claim 1, and an agriculturally acceptable carrier.

5. The purified polypeptide of claim 1 comprising an amino acid sequence selected from the group consisting of SEQ ID NOs: 8, 11, 14, 17, 20, 23 and 26.

6. An insecticidal composition comprising an insecticidally effective amount of the purified polypeptide of claim 5, and an agriculturally acceptable carrier.

7. A method of treating an insect or an insect larva, comprising contacting the insect, the insect larva, or the insect's environment with an insecticidally effective amount of a U-ACTX polypeptide, wherein the U-ACTX polypeptide comprises an amino acid sequence that is greater than or equal to about 90% identical to SEQ ID. NO: 2, wherein the U-ACTX polypeptide has insecticidal activity.

8. The method of claim 7 wherein the U-ACTX polypeptide comprises an amino acid sequence selected from the group consisting of SEQ ID. NOs: 9, 12, 15, 18, 24, 24 and 27.

* * * * *